(12) United States Patent
Hirota et al.

(10) Patent No.: US 9,507,291 B2
(45) Date of Patent: Nov. 29, 2016

(54) MAGNETIC PERMEABILITY DETECTOR, DEVELOPING DEVICE, IMAGE FORMING APPARATUS, AND OSCILLATION SIGNAL FREQUENCY CALCULATION METHOD THEREFOR

(71) Applicants: Tetsuro Hirota, Kanagawa (JP);
Hiroshi Hosokawa, Kanagawa (JP);
Shunji Katoh, Kanagawa (JP);
Masayuki Yamane, Kanagawa (JP);
Masahiro Watanabe, Kanagawa (JP);
Shingo Nishizaki, Kanagawa (JP)

(72) Inventors: Tetsuro Hirota, Kanagawa (JP);
Hiroshi Hosokawa, Kanagawa (JP);
Shunji Katoh, Kanagawa (JP);
Masayuki Yamane, Kanagawa (JP);
Masahiro Watanabe, Kanagawa (JP);
Shingo Nishizaki, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/887,025

(22) Filed: Oct. 19, 2015

(65) Prior Publication Data
US 2016/0041495 A1    Feb. 11, 2016

Related U.S. Application Data

(63) Continuation of application No. 14/256,141, filed on Apr. 18, 2014, now Pat. No. 9,170,233.

(30) Foreign Application Priority Data

| Apr. 23, 2013 | (JP) | 2013-090443 |
| Jun. 4, 2013 | (JP) | 2013-118324 |
| Oct. 1, 2013 | (JP) | 2013-206791 |
| Mar. 31, 2014 | (JP) | 2014-072830 |

(51) Int. Cl.
*G03G 15/08* (2006.01)
*G01N 27/72* (2006.01)

(52) U.S. Cl.
CPC .......... *G03G 15/0829* (2013.01); *G01N 27/72* (2013.01); *G03G 15/0848* (2013.01); *G03G 15/0853* (2013.01)

(58) Field of Classification Search
CPC .......... G03G 15/556; G03G 15/0856; G03G 15/0824; G03G 15/086; G03G 15/0831
USPC .......................................................... 399/27
See application file for complete search history.

(56) References Cited

U.S. PATENT DOCUMENTS 3,946,200 A * 3/1976 Juodikis ............. G05D 23/1909
                                                         219/497
4,987,449 A     1/1991 Katoh
(Continued)

FOREIGN PATENT DOCUMENTS

| JP | 6-175491 | 6/1994 |
| JP | 11-223620 | 8/1999 |

(Continued)

OTHER PUBLICATIONS

Machine translation of Ono JP 2010-026031 A, publication date: Feb. 4, 2010.*
Extended Search Report issued Nov. 13, 2014 in European Patent Application No. 14165558.9.
(Continued)

*Primary Examiner* — Walter L Lindsay, Jr.
*Assistant Examiner* — Frederick Wenderoth
(74) *Attorney, Agent, or Firm* — Oblon, McClelland, Maier & Neustadt, L.L.P.

(57) ABSTRACT

A magnetic permeability detector includes an LC oscillator circuit including a coil and a capacitor; and a resistor connected in series with the coil.

24 Claims, 27 Drawing Sheets

(56) References Cited

U.S. PATENT DOCUMENTS

| | | | |
|---|---|---|---|
| 6,021,050 A * | 2/2000 | Ehman | H05K 1/162 |
| | | | 174/255 |
| 6,212,343 B1 | 4/2001 | Hosokawa et al. | |
| 6,417,771 B1 | 7/2002 | Tyren | |
| 6,437,652 B1 * | 8/2002 | Gomez | H03B 5/364 |
| | | | 331/105 |
| 2004/0223782 A1 | 11/2004 | Hosokawa et al. | |
| 2006/0176350 A1 | 8/2006 | Howarth | |
| 2007/0086797 A1 | 4/2007 | Watanabe | |
| 2007/0194225 A1 | 8/2007 | Zorn | |
| 2007/0280725 A1 | 12/2007 | Hosokawa et al. | |
| 2011/0043589 A1 | 2/2011 | Hirota et al. | |
| 2011/0107832 A1 * | 5/2011 | Sakuma | G01F 1/6842 |
| | | | 73/204.26 |
| 2011/0176820 A1 | 7/2011 | Kadota et al. | |
| 2011/0182626 A1 | 7/2011 | Hirota et al. | |
| 2011/0194979 A1 * | 8/2011 | Chin | G01N 33/58 |
| | | | 422/69 |
| 2011/0229224 A1 | 9/2011 | Watanabe | |
| 2012/0095308 A1 | 4/2012 | Higuchi | |
| 2012/0200871 A1 | 8/2012 | Takahashi et al. | |
| 2012/0269532 A1 | 10/2012 | Watanabe | |
| 2013/0064570 A1 | 3/2013 | Yamane et al. | |

FOREIGN PATENT DOCUMENTS

| | | |
|---|---|---|
| JP | 2000-275951 | 10/2000 |
| JP | 2006-293282 | 10/2006 |
| JP | 2007-072123 | 3/2007 |
| JP | 2008-203064 | 9/2008 |
| JP | 2010-026031 | 2/2010 |

OTHER PUBLICATIONS

"(LC oscillators / 4.15), (Quartz-crystal oscillators /4.16), (Radio frequency circuit elements / 13.12 / Oscillators); (LC Butterworth filters/Appendix H)" In: Paul Horowitz, Winfield Hill: "The art of electronics", Jan. 1, 1986, Press Syndicate of the University of Cambridge, XP002731336, pp. 166-169, 570-573, 654-656 (12 pages).

Machine translation of Ono, JP 2010-026031 A, publication date: Feb. 4, 2010.

Machine translation of Anzai, JP 56067872 A, publication date: Jun. 8, 1981.

Combined Chinese Office Action and Search Report issued on May 5, 2016 in Patent Application No. 201410163099.7 (with English language translation of categories of cited documents).

Office Action mailed Jan. 25, 2016, co-pending U.S. Appl. No. 14/886,986.

* cited by examiner

MAGNETIC PERMEABILITY DETECTOR, DEVELOPING DEVICE, IMAGE FORMING APPARATUS, AND OSCILLATION SIGNAL FREQUENCY CALCULATION METHOD THEREFOR

CROSS-REFERENCE TO RELATED APPLICATIONS

This application is a continuation of U.S. patent application Ser. No. 14/256,141 filed on Apr. 18, 2014, which is based on and claims the benefit of priority pursuant to 35 U.S.C. §119 to Japanese Patent Application Nos. 2013-090443 filed on Apr. 23, 2013, 2013-118324 filed on Jun. 4, 2013, 2013-206791 filed on Oct. 1, 2013 and 2014-072830 filed on Mar. 31, 2014 in the Japan Patent Office. The entire disclosure of each of which is hereby incorporated by reference herein.

BACKGROUND OF THE INVENTION

Technical Field

Embodiments of the present invention generally relate to a magnetic permeability detector, a developer density detector, a developing device, and an image forming apparatus, such as, a copier, a printer, a facsimile machine, a plotter, or a multifunction peripheral (MFP) having at least two of coping, printing, facsimile transmission, plotting, and scanning capabilities; and further relates to a method of calculating a frequency of an oscillation signal.

Description of the Background Art

There are sensors that employ an LC oscillator circuit including a coil provided on a plane and detect magnetic permeability of space opposed to the plane on which the coil is provided (hereinafter "coil formation face") according to the frequency of signals output from the LC oscillator circuit. For example, in JP-H11-223620-A, such a sensor is used to detect the density of developer including magnetic substances inside a container in an electrophotographic image forming apparatus. The principle of such magnetic permeability sensors is based on that the inductance of coil changes depending on the magnetic permeability of a magnetic material to be detected. The inductance of coil changes due to changes in physical properties, such as magnetic permeability and conductivity, of the magnetic substance and changes in the distance to the magnetic material. The magnetic permeability in a range in which the magnetic flux of the magnetic permeability sensor acts can be detected by reading the oscillation frequency of the LC oscillator circuit dependent on inductance changes. In JP-H11-223620-A, further a resistance component of the circuit is considered in addition to respective elements of the circuit for designing with a higher degree of accuracy.

SUMMARY OF THE INVENTION

In view of the foregoing, one embodiment of the present invention provides a magnetic permeability detector that includes an LC oscillator circuit including a coil and a capacitor; and a resistor connected in series with the coil.

In another embodiment, a developing device includes a developer container to contain developer; and a developer density detector including a magnetic permeability detector to detect a density of developer in the developer container. The magnetic permeability detector includes an LC oscillator circuit including a coil and a capacitor; a resistor connected in series with the coil; an output terminal to output a signal having a frequency corresponding to a magnetic permeability in a range of action of a magnetic flux generated by a coil. The magnetic permeability detector is attached to the developing device so that the magnetic flux acts on the developer container.

Yet in another embodiment, an image forming apparatus include an image bearer, the developing device described above, and a controller including an oscillation circuit to generate a reference clock.

Yet another embodiment provides a method of calculating a frequency of an oscillation signal. The method includes a step of generating an interrupt signal at frequency calculation intervals; a step of acquiring a count value of the oscillation signal and a count value of a reference clock in response to the interrupt signal; a step of recognizing the frequency calculation interval based on the count value of the reference clock; and a step of calculating the frequency of the oscillation signal during the recognized frequency calculation interval using the count value of the oscillation signal.

BRIEF DESCRIPTION OF THE SEVERAL VIEWS OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
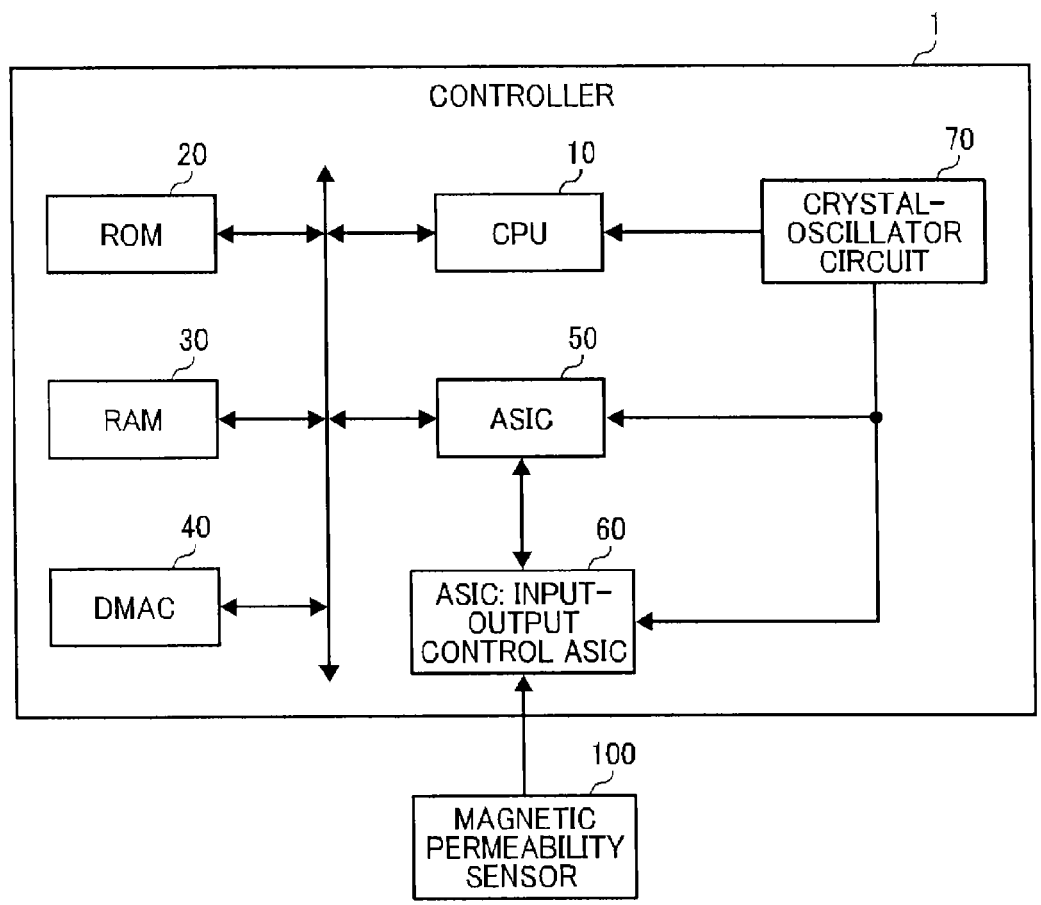
FIG. 1 is a schematic functional block diagram of a controller of an apparatus including a magnetic permeability sensor according to a first embodiment of the present invention.

In describing preferred embodiments illustrated in the drawings, specific terminology is employed for the sake of clarity. However, the disclosure of this patent specification is not intended to be limited to the specific terminology so selected, and it is to be understood that each specific element includes all technical equivalents that operate in a similar manner and achieve a similar result.

Typically, the frequency of signals output from LC oscillator circuits is responsive to environmental temperature or ambient temperature since properties of respective elements constituting the circuit change in response to changes in temperature. It is generally known that, in LC oscillator circuits, the frequency fluctuates in response to temperature changes like a quadric having a negative coefficient on a graph in which the abscissa represents the temperature and the ordinate represents the frequency.

To enhance the detection accuracy of magnetic permeability, it is preferable that the LC oscillator circuit depends on only the magnetic permeability inside the range in which the magnetic flux of the magnetic permeability sensor acts (a predetermined space opposed to the coil formation face). Accordingly, it is preferred to reduce fluctuations in frequency dependent on temperature, and it is desirable to adjust temperature characteristics of the LC oscillator circuit.

Although the temperature characteristics of the oscillation frequency by the LC oscillator circuit is determined by temperature dependent properties of the respective elements included in the circuit as described above, LC oscillator circuits typically include a coil and a capacitor, which affect the frequency to be output. Thus, freely adjusting them is difficult. Similarly, freely adjusting a circuit resistance, which can affect the temperature characteristics of the frequency, is difficult since the circuit resistance is determined by the entire circuit structure.

In view of the foregoing, an aim of the embodiment described below is to provide a magnetic permeability sensor capable of adjusting temperature characteristics of an LC oscillator circuit.

First Embodiment

Referring now to the drawings, wherein like reference numerals designate identical or corresponding parts throughout the several views thereof, and particularly to FIG. 1, a first embodiment of the present invention is described.

FIG. 1 is a schematic block diagram of a controller 1 of an apparatus including a magnetic permeability sensor 100 according to the present embodiment.

As shown in FIG. 1, the controller 1 according to the present embodiment has a configuration similar to that of typical data processing devices such as computers and servers. That is, the controller 1 includes a central processing unit (CPU) 10, a read only memory (ROM) 20, a random access memory (RAM) 30, a direct memory access controller (DMAC) 40, an application specific integrated circuit (ASIC) 50, an input-output control ASIC 60, and a crystal-oscillator circuit 70.

The CPU 10 is a computation unit and controls operation of the controller 1 entirely. The ROM 20 is a nonvolatile memory medium dedicated to reading out and stores programs such as firmware. The RAM 30 is a volatile memory medium capable of high-speed data reading and writing. The RAM 30 is used as workspace when the CPU 10 processes data. The DMAC 40 controls direct access to the RAM 30 without intervention of the CPU 10.

The ASIC 50 functions as a connection interface between a system bus to which the CPU 10 and the RAM 30 are connected and another device. The input-output control ASIC 60 acquires detection signals output from the magnetic permeability sensor 100 and converts the signals into data processable inside the controller 1. That is, the magnetic permeability sensor 100 is used as a magnetic permeability detector. The crystal-oscillator circuit 70 generates a reference clock to operate respective elements inside the controller 1.

Figure 2:
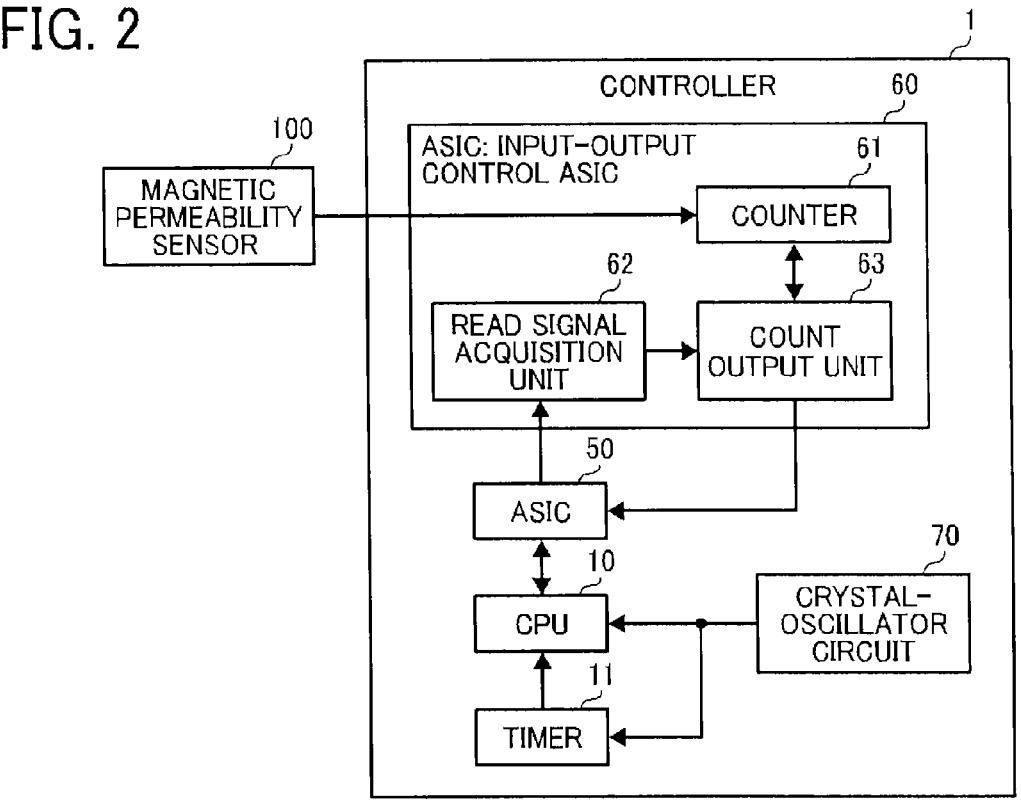
FIG. 2 is a schematic block diagram of an interface to process output signals from the magnetic permeability sensor shown in FIG. 1.

FIG. 2 is a functional block diagram illustrating the input-output control ASIC 60 in the controller 1 according to the present embodiment.

In the configuration shown in FIG. 2, the input-output control ASIC 60 includes a counter 61, a read signal acquisition unit 62, and a count output unit 63. The magnetic permeability sensor 100 according to the present embodiment is an oscillator circuit that outputs rectangular waves at the frequency corresponding to the magnetic permeability in a space to be detected. The counter 61 increments the value according to the rectangular wave output from the magnetic permeability sensor 100.

The read signal acquisition unit 62 acquires, via the ASIC 50, a read signal from the CPU 10. The read signal is a command to acquire the count value of the counter 61. Acquiring the read signal from the CPU 10, the read signal acquisition unit 62 inputs, to the count output unit 63, a signal instructing output of the count value. According to the signal input by the read signal acquisition unit 62, the count output unit 63 outputs the count value of the counter 61.

As shown in FIG. 2, the controller 1 includes a timer 11. The timer 11 outputs an interrupt signal to the CPU 10 each time the count of reference clock input from the crystal-oscillator circuit 70 reaches a predetermined count. The CPU 10 outputs the above-described read signal in response to the interrupt signal input from the timer 11.

It is to be noted that the CPU 10 has an access to the input-output control ASIC 60, for example, via a register. Accordingly, the above-described read signal is executed by writing, with the CPU 10, a value in a predetermined register included in the input-output control ASIC 60. Additionally, output of the count value from the count output unit 63 is executed by storing the count value in a predetermined register included in the input-output control ASIC 60 and acquiring the count value with the CPU 10.

Next, descriptions are given below of internal configuration of the magnetic permeability sensor 100 according to the present embodiment with reference to FIG. 3.

Figure 3:
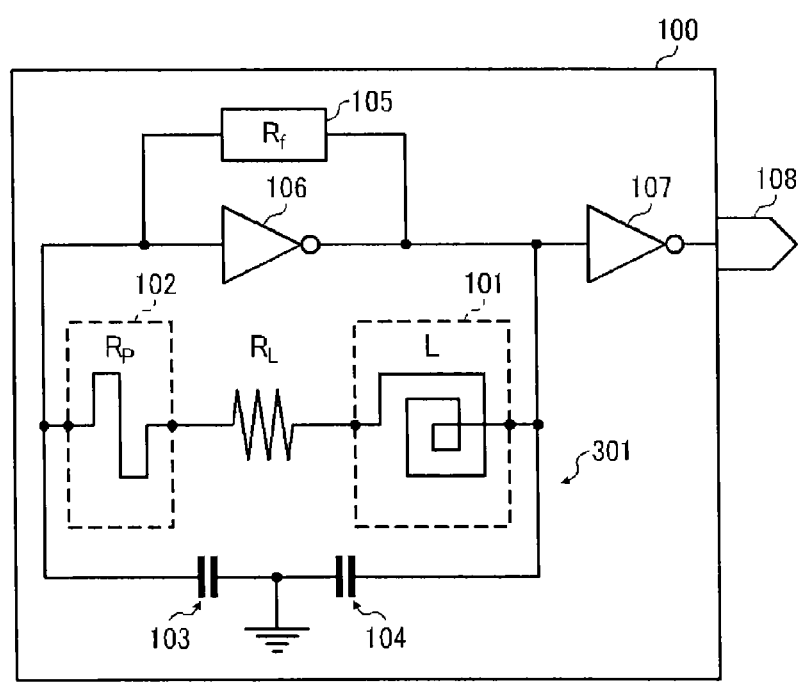
FIG. 3 is a schematic diagram illustrating circuitry of the magnetic permeability sensor shown in FIG. 1.

As shown in FIG. 3, the magnetic permeability sensor 100 according to the present embodiment is an oscillator circuit based on a Colpitts-type LC oscillator circuit 301 and includes a planar coil pattern 101, serving as a planar coil, first and second capacitors 103 and 104 serving as capacitors, a feedback resistor 105, an unbuffered integrated circuits (ICs) 106 and 107, and an output terminal 108. The magnetic permeability sensor 100 is further provided with an adjusting resistor 102, which is described later.

The coil pattern 101 is a planar coil constructed of conducting wire (signal wire) printed on a first face of a board 300 (shown in FIGS. 10A and 10B) constructing the magnetic permeability sensor 100. As shown in FIG. 3, the coil pattern 101 has an inductance L attained by the coil. In the coil pattern 101, the inductance L changes depending on the magnetic permeability of a space opposed to the first face on which the coil is provided (i.e., a coil formation face). That is, the inductance L depends on the magnetic permeability inside a range in which the magnetic flux of the magnetic permeability sensor 100 acts (range of action of the magnetic flux). As a result, the magnetic permeability sensor 100 outputs signals at the frequency corresponding to the magnetic permeability of the space opposed to the first face (hereinafter also "detection face").

Figure 10A:
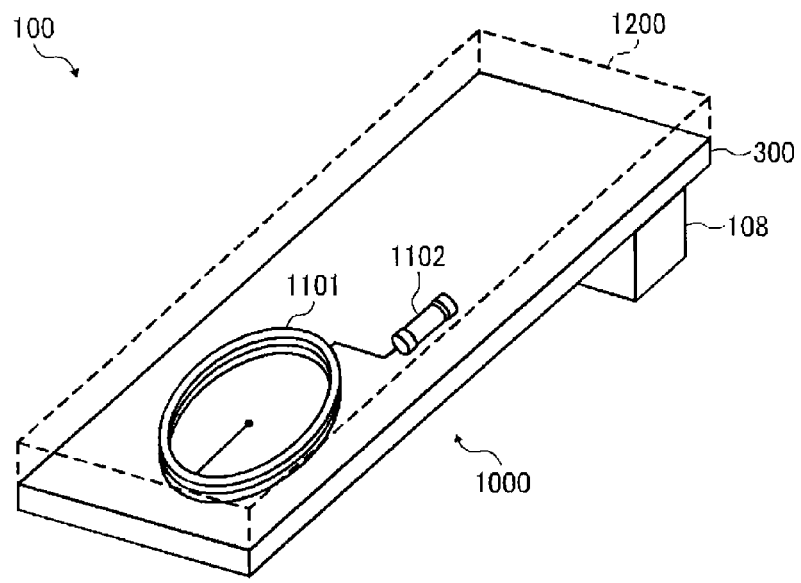
FIGS. 10A and 10B are schematic views of variations the coil and a resistor according to the first embodiment.
Figure 10B:
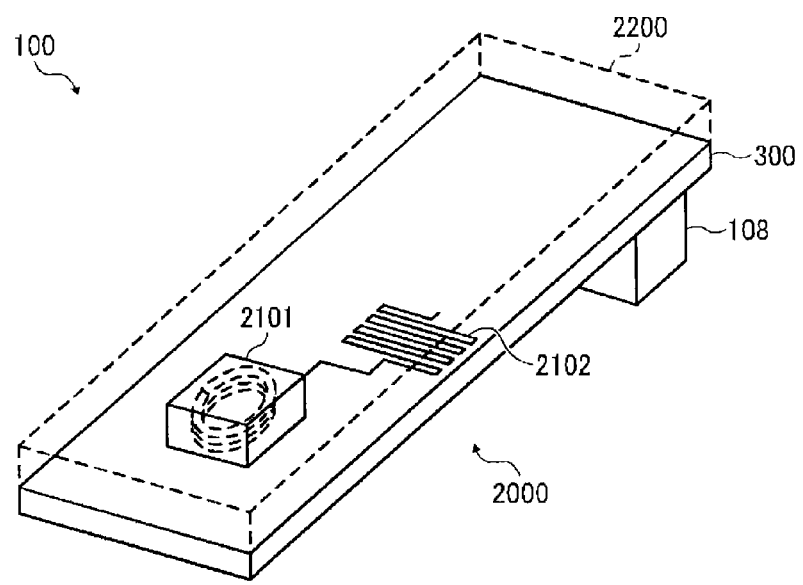

FIGS. 10A and 10B illustrating magnetic permeability sensors 1000 and 2000, respectively.

Although the planer coil pattern is used in the description above, the coil of the magnetic permeability sensor 100 is not limited thereto. For example, a coil 1101 constructed of coiled wire shown in FIG. 10A and a laminated chip coil 2101 shown in FIG. 10B can be used instead. When the coil 1101 shown in FIG. 10A is used, it is preferable to provide a cover 1200 to cover the face of the magnetic permeability sensor 1000 attached to the object detected so that the magnetic permeability sensor 1000 is not attached to the object in a tilted posture due to the difference in thickness between the coil 1101 and other portions than the coil 1101. When the laminated chip coil 2101 is used, used of a cover 2200 is preferable as well.

It is to be noted that reference numerals 1102 shown in FIG. 10A represents a resistor element, and 2102 shown in FIG. 10B represents an adjusting resistor.

The first and second capacitors 103 and 104 are capacitors that constitute the Colpitts-type LC oscillator circuit 301 together with the coil pattern 101. Accordingly, the first and second capacitors 103 and 104 are connected serially to each other and in parallel to the coil pattern 101. A resonance current loop is constructed by connecting the coil pattern 101 and the first and second capacitors 103 and 104 into a loop.

The feedback resistor 105 is inserted to stabilize a bias voltage. With a function of the unbuffered ICs 106 and 107, fluctuations in potential of a part of the resonance current loop are output from the output terminal 108 as a rectangular wave corresponding to the resonance frequency. With this configuration, the magnetic permeability sensor 100 oscillates at the frequency corresponding to the inductance L, a capacitance C of the first and second capacitors 103 and 104, and a circuit resistance $R_L$ described later. It is to be noted that it is preferred that elements including the first and second capacitors 103 and 104, the feedback resistor 105, the unbuffered ICs 106 and 107, and the output terminal 108 be provided to the opposite face of the board 300 from the face on which the coil pattern 101 is provided. Additionally, those elements are preferably surface-mounted (SMT) to avoid unnecessary projections on the face on which the coil pattern 101 is provided. This is because detection errors arise if the coil pattern 101 that is a detecting portion is not positioned accurately relative to the detected object.

The inductance L changes depending on the presence of the magnetic material adjacent to the coil pattern 101 (planar coil) and also the density thereof. Accordingly, the magnetic permeability in the space adjacent to the coil pattern 101 can be detected with the oscillation frequency of the magnetic permeability sensor 100. Further, to design the oscillation frequency of the magnetic permeability sensor 100 with a higher degree of accuracy, also considered is the circuit resistance $R_L$ caused by the conducting wire (signal wire) constituting the circuit as shown in FIG. 3. The frequency in accordance with parameters of the respective components constituting the magnetic permeability sensor 100 is described later.

Figure 4:
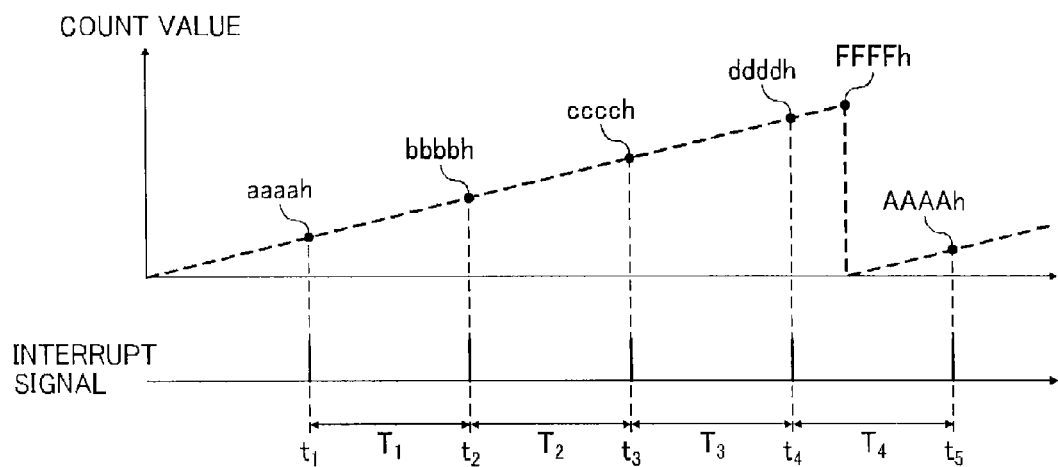
FIG. 4 is a chart illustrating count values in the magnetic permeability sensor shown in FIG. 3.

FIG. 4 is a chart illustrating count by the function of the input-output control ASIC 60 of the magnetic permeability sensor 100.

If there are no changes in the density of the magnetic material adjacent to the magnetic permeability sensor 100, the magnetic permeability sensor 100 oscillates at a constant frequency basically. Consequently, the count value of the counter 61 increases constantly with elapse of time as shown in FIG. 4.

Additionally, receiving the interrupt signal from the timer 11, the CPU 10 outputs the read signal to the input-output control ASIC 60 and acquires the count value of the counter 61 at that time. For example, in FIG. 4, at time points $t_1$, $t_2$, $t_3$, $t_4$, and $t_5$, count values aaaah, bbbbh, ccch, ddddh, and AAAAh are acquired respectively.

Acquiring the count values at the respective time points, the CPU 10 calculates the frequency in periods $T_1$, $T_2$, $T_3$, and $T_4$ shown in FIG. 4, respectively. The timer 11 in the present embodiment outputs the interrupt signal when counting the reference clock for an amount equivalent of 2 milliseconds (ms). Accordingly, the CPU 10 divides the count values of the counter 61 in the respective periods with 2 (ms), thereby calculating an oscillation frequency f (Hz) of the magnetic permeability sensor 100 in the periods $T_1$, $T_2$, $T_3$, and $T_4$ respectively.

Additionally, as shown in FIG. 4, the upper limit of the count of the counter 61 is FFFFh in the present embodiment. Accordingly, in calculating the oscillation frequency f (Hz) in the period $T_4$, the CPU 10 divides with 2 (ms) the sum of the AAAAh and a value obtained by deducting ddddh from FFFFh.

Figure 5:
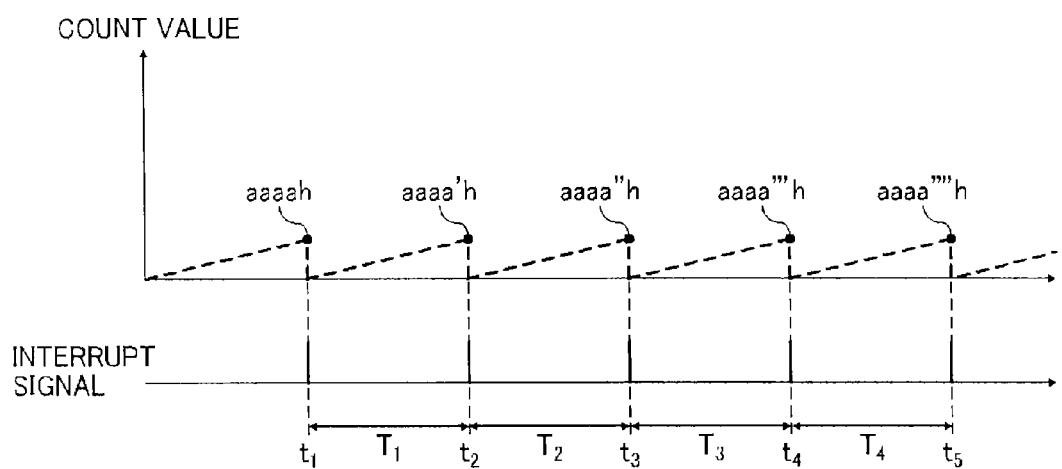
FIG. 5 is a chart illustrating another example of count values in the magnetic permeability sensor shown in FIG. 3.

FIG. 5 is a chart illustrating another example of count by the input-output control ASIC 60 of the magnetic permeability sensor 100.

In the case of FIG. 5, in the input-output control ASIC 60, the counter 61 resets the count value after the count output unit 63 reads out the count value. For the resetting, the count output unit 63 may input a reset signal to the counter 61 after reading out the count value. Alternatively, the counter 61 may include a capability to resetting the count value each time the count value is read out.

In the configuration shown in FIG. 5, the count values acquired at the respective time points are the values counted in the periods $T_1$, $T_2$, $T_3$, and $T_4$, respectively. Accordingly, the CPU 10 divides with 2 (ms) the count value acquired at each timing, thereby calculating the oscillation frequency f (Hz).

Thus, the controller 1 according to the present embodiment acquires the frequency of signals oscillated by the magnetic permeability sensor 100 and can determine, based on the result of acquisition, a phenomenon corresponding to the oscillation frequency of the magnetic permeability sensor 100. Then, in the magnetic permeability sensor 100, the inductance L changes in response to the density of the magnetic material present in the space opposed to the coil pattern 101, and the frequency of signals output from the output terminal 108 changes. Consequently, the controller 1 can detect the density of magnetic material in the space opposed to the coil pattern 101 on the detection face.

The magnetic permeability sensor 100 oscillates at the frequency corresponding to the density of magnetic material in the above-described predetermined space. By contrast, the crystal-oscillator circuit 70 oscillates at a predetermined frequency. Further, the magnetic permeability sensor 100 and the crystal-oscillator circuit 70 both are dependent on temperature, that is, the oscillation frequency thereof fluctuates in accordance with ambient temperature.

Figure 6:
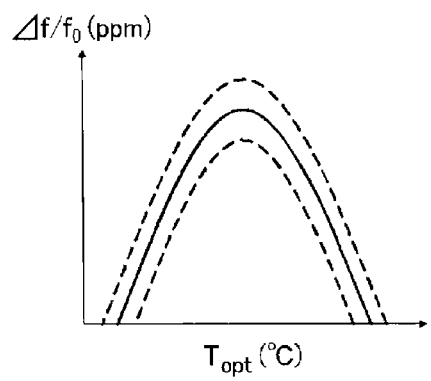
FIG. 6 is a graph illustrating temperature characteristics of oscillation frequency of a crystal-oscillator circuit according to the first embodiment.

FIG. 6 is a graph illustrating temperature characteristics of the crystal-oscillator circuit 70. As shown in FIG. 6, the crystal-oscillator circuit 70 has temperature characteristics such that the frequency thereof draws a parabola with the peak thereof at a certain temperature.

In the controller 1, it is preferred to reduce relative changes of the oscillation frequency of the magnetic permeability sensor 100 and that of the crystal-oscillator circuit 70 caused by temperature changes to accurately detect the density of magnetic material in the predetermined space based on the frequency of signals generated by oscillation of the magnetic permeability sensor 100. Additionally, as described above, the controller 1 calculates the oscillation frequency by acquiring, at each 2 ms, the count value counted by the timer 11 and dividing the count value with 2.

Herein, the timer 11 counts 2 ms according to the reference clock input from the crystal-oscillator circuit 70. Accordingly, if the oscillation frequency fluctuates due to the temperature characteristics shown in FIG. 6, the duration of counting 2 ms fluctuates as long as the count values for 2 ms are identical. This causes errors in oscillation frequency of the magnetic permeability sensor 100 calculated by the CPU 10.

If the temperature characteristics of the magnetic permeability sensor 100 are similar to that of the crystal-oscillator circuit 70 shown in FIG. 6, the above-described errors in calculation of the oscillation frequency can be canceled. That is, even if the oscillation frequency of the crystal-oscillator circuit 70 fluctuates due to temperature changes, fluctuations in the values counted by the counter 61 in the counting duration of 2 ms can be smaller as long as the oscillation frequency of the magnetic permeability sensor 100 displays similar fluctuations. Accordingly, errors can be smaller in the subsequent calculation of the oscillation frequency of the magnetic permeability sensor 100.

Thus, the density of magnetic material in the predetermined space can be detected with a higher degree of accuracy based to the frequency of signals oscillated by the magnetic permeability sensor 100. Accordingly, it is preferred that the temperature characteristics of the oscillation frequency of the magnetic permeability sensor 100 be adjustable to resemble the temperature characteristics of the oscillation frequency of the crystal-oscillator circuit 70.

Descriptions are given below of distinctive features of the magnetic permeability sensor 100 according to the present embodiment.

In the magnetic permeability sensor 100, upon application of power supply voltage, electrical current (hereinafter simply "current") flows through the coil pattern 101 and causes a magnetic flux in a predetermined direction. Then, the magnetic permeability sensor 100 outputs, from the output terminal 108, a signal having a frequency corresponding to the magnetic permeability in the range of action of the magnetic flux.

Initially, an oscillation frequency $f_0$ of the LC oscillator circuit 301 is described below. When the circuit resistance $R_L$ caused by the conducting wire and the like constructing the circuit is considered, the oscillation frequency $f_0$ of the LC oscillator circuit. 301 can be expressed as follows.

$$f_0 = \frac{1}{2\pi\sqrt{LC}}\sqrt{1 - R_L^2\frac{C}{4L}} \quad \text{Formula 1}$$

Accordingly, the oscillation frequency of the magnetic permeability sensor 100 is expressed with a function of the inductance L attained by the coil pattern 101, the capacitance C of the first and second capacitors 103 and 104 (i.e., capacitor), and the circuit resistance $R_L$. Therefore, in adjusting the temperature characteristics of the oscillation frequency of the magnetic permeability sensor 100, the parameters "L", "C", and "$R_L$" included in formula 1 are considered.

Figure 7:
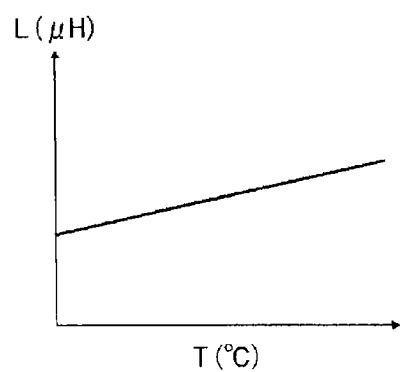
FIG. 7 is a graph illustrating temperature characteristics of inductance of coil according to the first embodiment.

FIG. 7 is a graph illustrating the temperature characteristics of the inductance L of the coil pattern 101. Referring to FIG. 7, as the board 300 (printed circuit board) expands in response to temperature rise, the coil size increases, and accordingly the inductance L of the coil pattern 101 increases.

Figure 8:
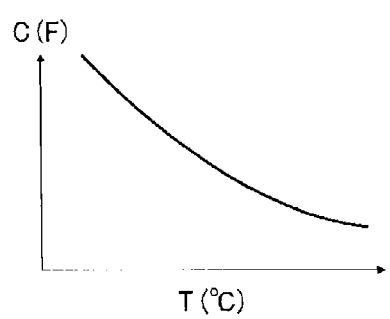
FIG. 8 is a graph illustrating temperature characteristics of a capacitor according to the first embodiment.
Figure 9:
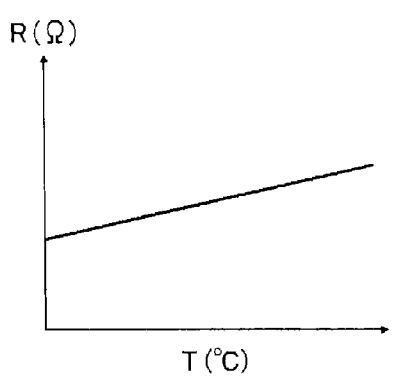
FIG. 9 is a graph illustrating temperature characteristics of a resistance according to the first embodiment.

FIG. 8 is a graph illustrating temperature characteristics of the capacitance C of the first and second capacitors 103 and 104. As shown in FIG. 8, the capacitance C of the first and second capacitors 103 and 104 decreases in response to temperature rise. FIG. 9 is a graph illustrating temperature characteristics of the circuit resistance $R_L$. As shown in FIG. 9, the circuit resistance $R_L$ increases in response to temperature rise.

The following advantages can be attained by adjusting the respective parameters while considering the temperature characteristics of the respective elements of the magnetic permeability sensor 100. That is, such adjustment can reduce, in the magnetic permeability sensor 100, fluctuations in the oscillation frequency caused by temperature fluctuations, make the temperature characteristics thereof similar to the temperature characteristics of the crystal-oscillator circuit 70 described with reference to FIG. 6, or attain both.

The inventors of the present application, however, recognize that adjusting the parameters "L", "C", and "$R_L$" included in formula 1 independently is difficult since those parameters are correlated to each other on the premise that the magnetic permeability detecting capability is established. Specifically, the circuit resistance $R_L$ is affected by the length of the conducting wire that changes in accordance with the number of coil winding of the coil pattern 101, the inductance L of the coil pattern 101 is determined by the number of coil winding, and the number of coil winding affects the sensing capability of the magnetic permeability sensor 100.

In view of the foregoing, in the present embodiment, the magnetic permeability sensor 100 is further provided with the adjusting resistor 102 serving as a resistor (i.e., resistance adjusting portion) that does not affect the inductance L of the coil pattern 101, and the circuit resistance $R_L$ is adjustable by a resistance value $R_P$ of the adjusting resistor 102. With the adjusting resistor 102, the circuit resistance $R_L$ can be adjusted independently not to affect the inductance L, and thus the temperature characteristics can be adjusted without affecting the sensing capability of the magnetic permeability sensor 100.

The adjusting resistor 102 serving as the resistor according to the present embodiment is provided in series with the coil pattern 101 and parallel to the first and second capacitors 103 and 104 so that the adjusting resistor 102, together with the coil pattern 101 and the first and second capacitors 103 and 104, constitute the resonance current loop in the Colpitts-type LC oscillator circuit 301 of the magnetic permeability sensor 100.

It is to be noted that, although the adjusting resistor 102 is a planar resistance pattern in the present embodiment, alternatively, an independent resistor element 1102, which is smaller in variations in individual temperature characteristics, may be used instead as shown in FIG. 10A.

The adjusting resistor 102 is shaped in planar resistance pattern and constructed of conducting wire printed on the board 300, which is similar to the coil pattern 101. Although the resistance pattern (the adjusting resistor 102) can have various shapes, such as linear shapes and curved line shapes, a considerable length is required for the capability of resistor, thus making the sensor bulkier. In practice, a conducting wire piece having a length required for the capability of resistor is disposed inside a limited area of the board 300 except the range where the coil pattern 101 is present.

Figure 11A:
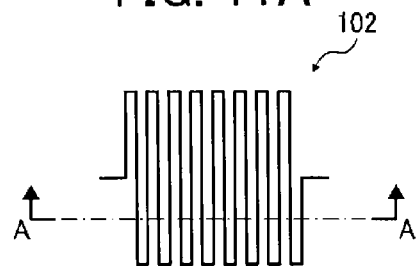
FIGS. 11A, 11B, 11C, and 11D are diagrams for understanding of a magnetic flux generated in a resistance pattern according to the first embodiment.
Figure 19A:
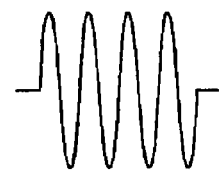
FIGS. 19A through 19D illustrate shapes of the resistance pattern according to another embodiment.
Figure 19B:
Figure 19C:
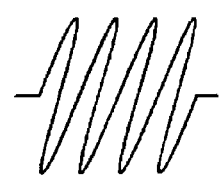
Figure 19D:

In view of the foregoing, in the present embodiment, the adjusting resistor 102 is constructed of conducting wire bent multiple times from one side to the opposite side, and vice versa, to reciprocate in the predetermined direction on the board 300. For example, the adjusting resistor 102 can be formed with straight lines and right angles as shown in FIG. 11A, sine curves as shown in FIG. 19A, or straight lines and acute angles as shown in FIG. 19B. Alternatively, as shown in FIGS. 19C and 19D, peaks and valleys in the shapes shown in FIGS. 19A and 19B may be inclined relative to the side of the board 300. In the descriptions below, the term "serpentine" means the above-described shape (may be called "zigzag") in which the straight or curved lines are bent and folded back multiple times to reciprocate in the predetermined direction.

For example, the planar coil pattern 101 and the adjusting resistor 102 are formed in the following manner.

Initially, plate front and back sides of a glass epoxy board (substrate), such as Flame retardant-4 (FR-4) and Composite epoxy material-3 (CEM-3), with copper foil in a predetermined thickness. Coat the plated board with dry film that hardens with light, thus forming two layers different in material on the front and back sides of the glass epoxy board. Subsequently, put a mask film with a circuit pattern laid thereon on the coated board, from above the dry film, in close contact with each other, and enhance the contact therebetween by vacuum suction, thereby fixing the mask film thereto. Expose the board to a predetermined amount of light having a predetermined wavelength for a predetermined duration. Then, the dry film does not harden in portions covered with the mask film and light is blocked. By contrast, the dry film hardens in portions exposed to light. In this state, subject the board in an etching liquid. Then, the masked portion, that is, the portion where the dry film does not harden, dissolves in the etching liquid. Simultaneously, the copper foil under it dissolves and is lost as well. In the exposed portion, which is not masked, the dry film does not dissolve and remains owing to the hardening, and the copper foil under it remains as well. Subsequently, remove the dry film. Then, only a minute pattern of copper foil with a width of about 100 µm remains on the board. As required, apply resist coat liquid entirely in a constant thickness and let the coat harden with heat to prevent pattern loss by oxidization or damage to the board. Thus, the coil pattern 101 and the adjusting resistor 102 can be printed on the board 300.

Incidentally, in a case where the planar coil pattern 101 is printed on the back side of the board 300 whereas the adjusting resistor 102 is printed on the front side of the board 300, in production of the printed circuit board, the front and back sides of the board 300 is exposed to different types of etching liquid via the board 300. That is, the concentration of the etching liquid for the front side and that for the back side are different from a partial standpoint although the board 300 is etched in a large vessel from a macro standpoint. Consequently, differences are caused in the etching conditions. Therefore, there is the possibility that the remaining dry film slightly differs in width (width of copper foil pattern) between the front side and the back side, and the temperature characteristics of the oscillation frequency of the magnetic permeability sensor 100 deviate from the target.

To avoid such factors to cause manufacturing variations, in the magnetic permeability sensor 100 according to the present embodiment, the coil pattern 101 and the adjusting resistor 102 are printed on an identical board face of the printed circuit board. It is to be noted that, as described above, the electronic elements such as the first and second capacitors 103 and 104 are preferably provided to the opposite face of the board 300 from the face on which the coil pattern 101 and the adjusting resistor 102 are printed so that the location of the coil pattern 101 can be proper relative to the detected object.

Additionally, the oscillation frequency f of the LC oscillator circuit 301 can be expressed by formula 2 below, in which the resistance value $R_P$ of the adjusting resistor 102 is considered.

$$f = \frac{1}{2\pi}\sqrt{\frac{1}{LC} - \left(\frac{R_L + R_P}{2L}\right)^2} \qquad \text{Formula 2}$$

Although it is difficult to adjust the parameters "$R_L$", "L", and "C" as described above, the resistance value $R_P$ can be adjusted independently. As described above with reference to FIG. 9, generally the resistance changes proportionally to temperature change, and accordingly the resistance value $R_P$ of the adjusting resistor 102 causes the oscillation frequency f to decrease according to temperature rise.

Next, descriptions are given below of a configuration to adjust the resistance value $R_P$ by the adjusting resistor 102 that is a planer resistor without affecting the inductance L of the coil pattern 101 with reference to FIGS. 11A through 11D.

Figure 11B:
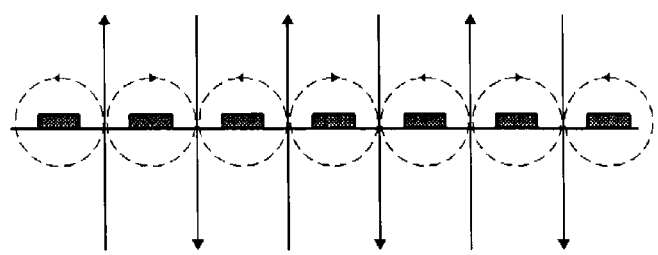

FIG. 11A illustrates a shape of the adjusting resistor 102, and FIG. 11B is a cross-sectional view along line A-A shown in FIG. 11A.

As shown in FIG. 11B, as a current flows through the adjusting resistor 102, magnetic fluxes are generated around the conducting wire as indicated by broken lines in the drawing according to the right hand rule regarding ampere. Since the magnetic flux increases in strength between the adjacent patterns (adjacent wire segments), between the adjacent patterns, a magnetic flux is generated in a direction perpendicular to the face on which the serpentine pattern is provided, as indicated by a solid line in FIG. 11C.

Figure 11C:
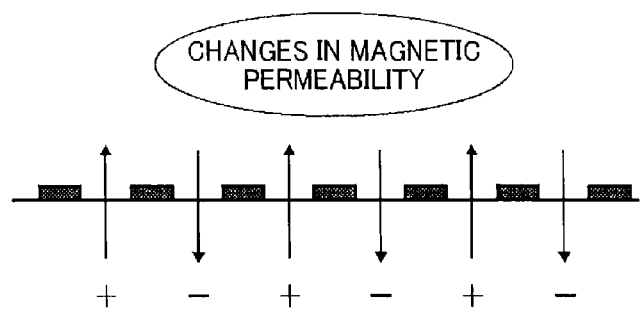

However, as shown in FIG. 11C, the direction of magnetic flux generated between an initial pair of adjacent wire segments is the opposite to the direction of magnetic flux generated between a subsequent pair of adjacent wire segments, and the direction alternate sequentially. Accordingly, the magnetic fluxes in the opposite directions cancel each other. Therefore, in the entire serpentine adjusting resistor 102, the magnetic flux perpendicular to the face on which the resistance pattern is provided is canceled.

The direction perpendicular to the face on which the serpentine adjusting resistor 102 is provided is identical to the direction in which the coil pattern 101 generates the magnetic flux. Thus, practically, the serpentine adjusting resistor 102 does not generate magnetic fluxes in the direction in which the magnetic flux of the coil pattern 101 is generated. Therefore, it can be deemed that the serpentine adjusting resistor 102 attains the resistance value $R_P$ that is not affected by the ambient magnetic permeability and does not have the capability to sense the magnetic permeability. In other words, this is a resistance value that does not affect the inductance L of the coil pattern 101.

Figure 11D:
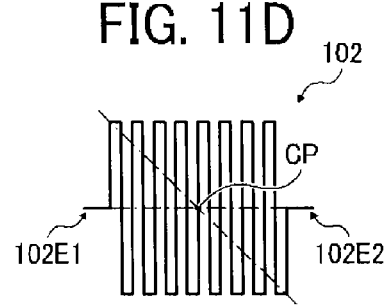

It is to be noted that, when the serpentine shape of the adjusting resistor 102 is symmetrical relative to a point so that the number of folding back from one side is identical to the number of folding back from the other side, the magnetic fluxes in the opposite directions can coincide with each other. More specifically, as shown in FIG. 11D, the adjusting resistor 102 has a serpentine shape symmetric with respect to a center point CP of a line connecting together a first end 102E1 and a second end 102E2 connected to the LC oscillator circuit 301. The adjusting resistor 102 can be serpentine in various manner as shown in FIGS. 16 and 19A through 19D. The shape shown in FIG. 16, in which the adjacent segments of conducting wire are parallel to each other, is advantageous in canceling the magnetic fluxes.

It is to be noted that, the magnetic permeability sensor 100 according to the present embodiment further includes a test wiring pattern 102' printed on the second face of the printed circuit board opposite the first face (i.e., detection face) on which the adjusting resistor 102 is printed. The test wiring pattern 102' is identical or similar in shape with the adjusting resistor 102. The resistance value $R_P$ of the adjusting resistor 102 is determined by measuring the resistance value of the test wiring pattern 102'. This is because measuring directly the resistance value of the adjusting resistor 102 may result in damage to the adjusting resistor 102 constituted of minute printed wiring, the coil pattern 101 in the same face of the board 300 as the adjusting resistor 102, or both.

Here, descriptions are given below of measurement of changes in the oscillation frequency of the magnetic permeability sensor 100 in response to temperature change while the resistance value $R_P$ of the adjusting resistor 102 in the configuration shown in FIG. 3 was varied. FIGS. 12A through 12D illustrates the results. It is to be noted that, the resistance values in FIGS. 12A through 12D are in relation of $R_{P1} < R_{P2} < R_{P3} < R_{P4}$.

Figure 12A:
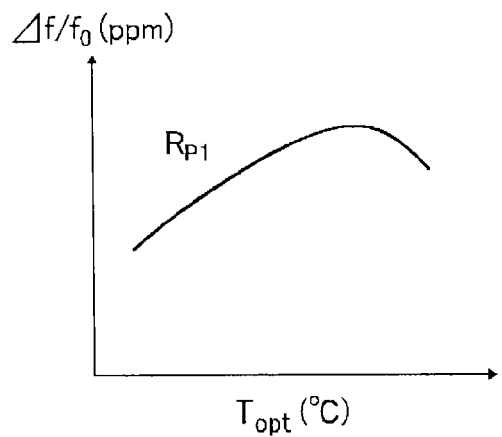
FIGS. 12A through 12D are graphs illustrating differences in temperature characteristics of oscillation frequency when multiple resistance values are used in the magnetic permeability sensor according to the first embodiment.
Figure 12B:
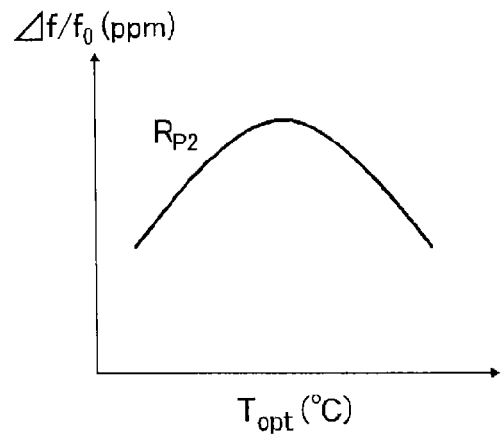
Figure 12C:
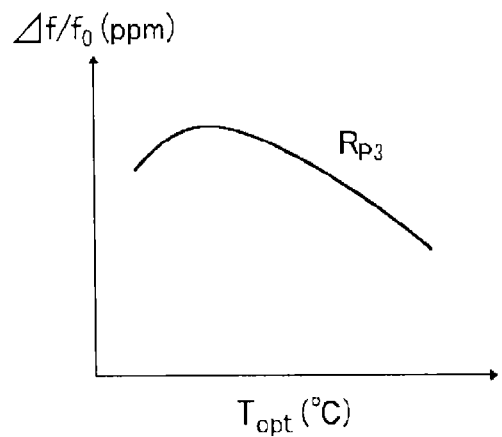
Figure 12D:
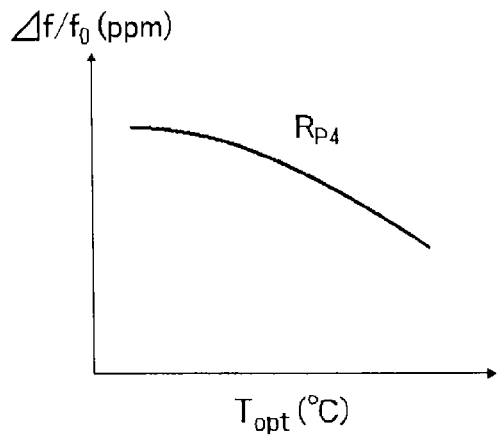
Figure 13A:
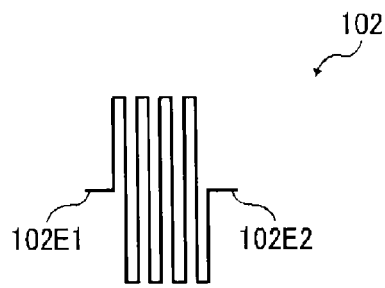
FIGS. 13A through 13D illustrate shapes of the resistance pattern included in the magnetic permeability sensor according to the first embodiment.
Figure 13B:
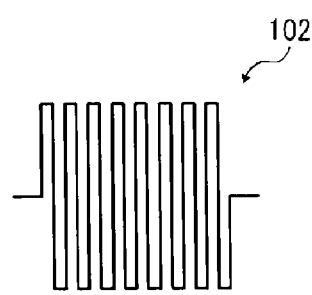
Figure 13C:
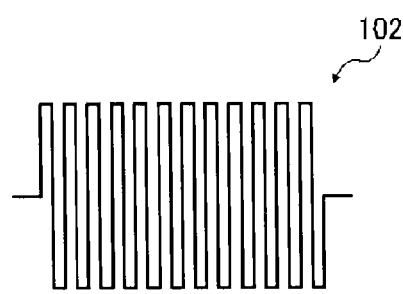
Figure 13D:
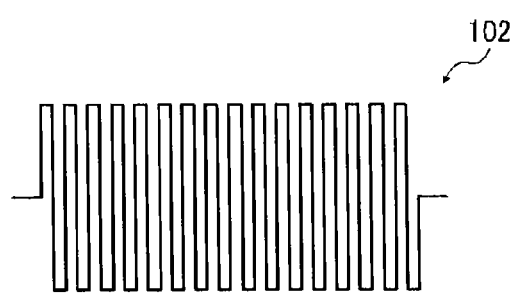

As shown in FIGS. 12A though 12D, the oscillation frequency of the magnetic permeability sensor 100 changes like a parabola in response to temperature change. As the resistance value $R_P$ increases, the peak temperature at which the oscillation frequency reaches a peak (extreme temperature) descends. Accordingly, it can be known that the temperature characteristics of the oscillation frequency of the magnetic permeability sensor 100 can be adjusted by changing the resistance value $R_P$ of the adjusting resistor 102.

Adjustment of the resistance value $R_P$ of the adjusting resistor 102 is described below. FIGS. 13A through 13D illustrate shapes of the adjusting resistor 102 that coincide with the resistance values $R_{P1}$ through $R_{P4}$ shown in FIGS. 12A through 12D.

Referring to FIGS. 13A through 13D, the resistance value $R_P$ can be increased by increasing the number of serpentine folding (the number of reciprocation from one side to the other side and vice versa) in the serpentine adjusting resistor 102. In other words, the resistance value $R_P$ added to the circuit resistance $R_L$ can be increased by increasing the number of serpentine folding. Then, the peak temperature at which the oscillation frequency of the magnetic permeability sensor 100 reaches its peak (extreme value) can be lowered without affecting the inductance L of the coil pattern 101.

As described above, the magnetic permeability sensor 100 can be produced with the temperature characteristics thereof made similar to preliminarily obtained temperature characteristics of the oscillation frequency of the crystal-oscillator circuit 70. With the magnetic permeability sensor 100 thus configured, even when the oscillation frequency of the crystal-oscillator circuit 70 fluctuates due to temperature changes, errors or differences in the oscillation frequency of the magnetic permeability sensor 100 calculated in the controller 1 can be reduced since the oscillation frequency of the magnetic permeability sensor 100 fluctuates similarly. Accordingly, this configuration can enhance the accuracy in detecting the magnetic permeability (density of magnetic material) inside the range of action of the magnetic flux of the magnetic permeability sensor 100 (the predetermined space opposed to the face on which the coil pattern 101 is provided).

It is to be noted that, in an experimental measurement in which ambient temperature (temperature of environment under which the magnetic permeability sensor 100 was used) was set to a range from 10° C. to 50° C., the oscillation frequency of the crystal-oscillator circuit 70 fluctuated ±10 to 40 part per million (ppm). When the resistance value $R_P$ of the adjusting resistor 102 was adjusted to cause the peak on the parabola like temperature characteristics of the magnetic permeability sensor 100 to coincide with the peak on the parabola like temperature characteristics of the crystal-oscillator circuit 70, they substantially coincided with each other at a resistance value of 0.3Ω.

In the experimental measurement with the temperature range of 10° C. to 50° C., the oscillation frequency of the magnetic permeability sensor 100 thus produced fluctuated ±37 ppm and generally coincided with the fluctuation range of frequency of the crystal-oscillator circuit 70, which was ±10 to 40 ppm.

As described above, the first embodiment above can provide a magnetic permeability sensor capable of adjusting temperature characteristics of an LC oscillator circuit 301.

In the magnetic permeability sensor 100 according to the above-described embodiment, by providing the adjusting resistor 102, serving as a resistance adjusting portion, in series to the coil pattern 101, serving as a detecting portion, in the resonance current loop of the Colpitts-type LC oscillator circuit 301, the temperature characteristics of the oscillation frequency can be adjusted to coincide with the temperature characteristics of the oscillator circuit that outputs the reference clock.

Second Embodiment

As a second embodiment, descriptions are given below of use of the above-described magnetic permeability sensor 100 to detect the density of toner inside a container. Toner is a developer contained in a developing device to develop an electrostatic latent image in an electrophotographic image forming apparatus.

Figure 14:
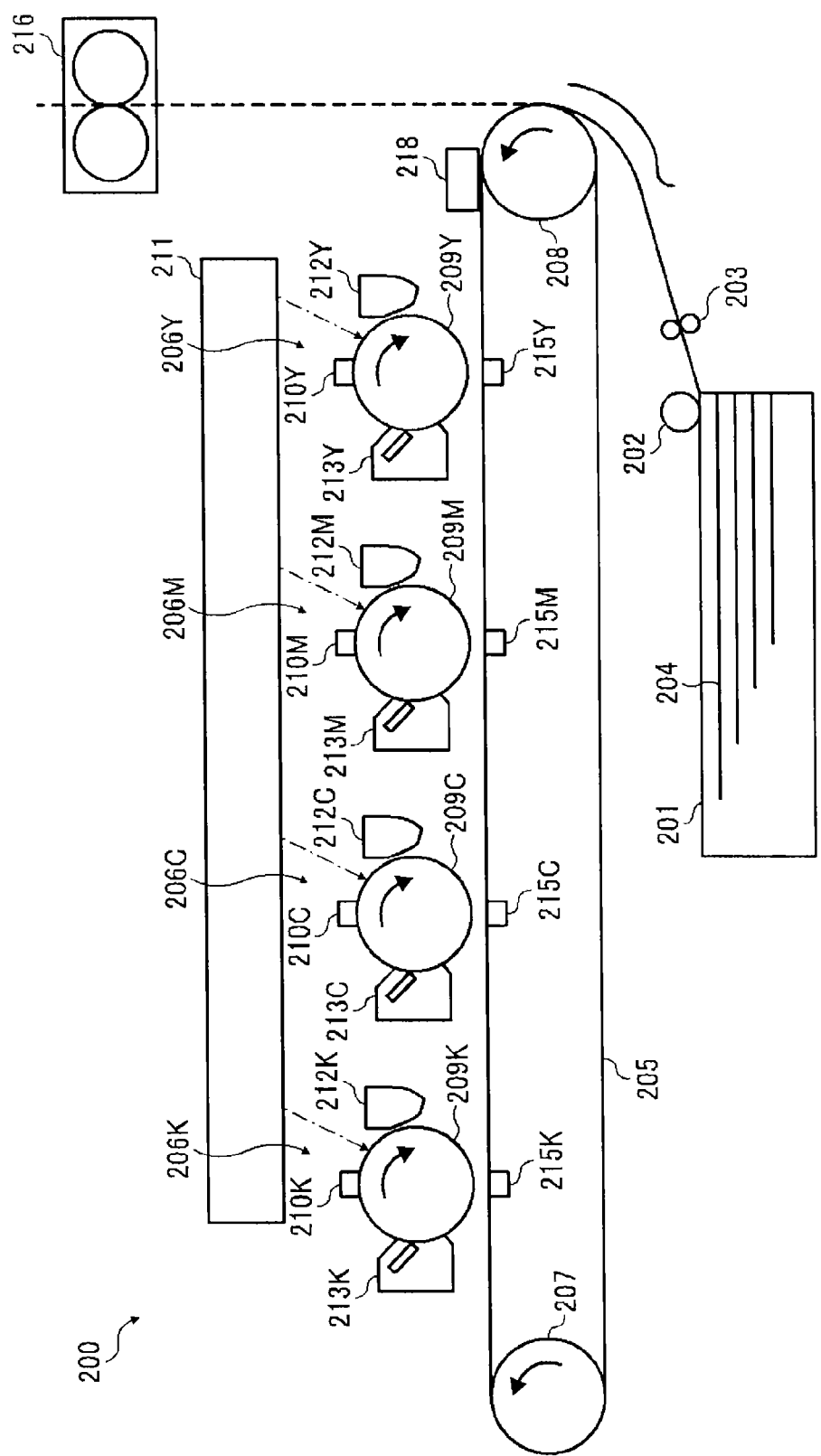
FIG. 14 illustrates a mechanical structure of an image forming apparatus according to a second embodiment, which includes a developing device provided with the magnetic permeability sensor shown in FIG. 3.

FIG. 14 is a side view illustrating a mechanism to form and output images, included in an image forming apparatus 200 according to the present embodiment.

The image forming apparatus 200 shown in FIG. 14 is a so-called tandem-type image forming apparatus and includes image forming units 206K, 206C, 206M, and 206Y for respective colors, arranged along a conveyance belt 205 that is an endless movable member. Specifically, the multiple image forming units 206Y, 206C, 206M, and 206Y (i.e., electrophotographic process units, hereinafter collectively "image forming units 206") are arranged in that order from the upstream side in a belt conveyance direction in which the conveyance belt 205 transports the image. In the image forming apparatus 200, sheets 204 of recording media are fed from a sheet tray 201 by a feed roller 202. On the conveyance belt 205, which is an intermediate transfer belt, an intermediate-transfer image to be transferred onto the sheet 204 is formed.

Additionally, a pair of registration rollers 203 stops the sheet 204 fed from the sheet tray 201 and forwards the sheet 204 to a secondary-transfer position where the image is transferred from the conveyance belt 205, timed to coincide with image formation in the image forming units 206.

The multiple image forming units 206 have a similar configuration except the color of toner images formed thereby. The image forming unit 206K forms black toner images, the image forming unit 206M forms magenta toner images, the image forming unit 206C forms cyan toner images, and the image forming unit 206Y forms yellow toner images.

The conveyance belt 205 is an endless belt looped around a driving roller 207 and a driven roller 208. A driving motor rotates the driving roller 207. The driving motor, the driving roller 207, and the driven roller 208 together constituting a driving unit to drive the conveyance belt 205.

Among the four image forming units 206, the image forming unit 206Y is the first to transfer toner images onto the conveyance belt 205. The image forming unit 206Y includes a photoreceptor drum 209Y and components disposed around the photoreceptor drum 209Y, namely, a charging device 210Y, an optical writing device 211, a developing device 212Y, a cleaning unit 213Y, and a discharger. The optical writing device 211 directs light to the photoreceptor drum 209Y, 209M, 209C, and 209K (collectively "photoreceptor drums 209").

To form images, the charging device 210Y charges uniformly the outer circumferential face of the photoreceptor drum 209Y in the dark, after which the optical writing device 211 directs light from a light source corresponding to yellow images to the photoreceptor drum 209Y, thus forming an electrostatic latent image thereon. The developing device 212Y develops the electrostatic latent image with yellow toner, thus forming a yellow toner image on the photoreceptor drum 209Y.

The toner image is transferred by a transfer device 215Y onto the conveyance belt 205 at a primary transfer position where the photoreceptor drum 209Y contacts or is closest to the conveyance belt 205. Thus, the yellow toner image is formed on the conveyance belt 205. Subsequently, the cleaning unit 213Y removes toner remaining on the outer circumferential face of the photoreceptor drum 209Y, and the discharger discharges the outer circumferential face of the photoreceptor drum 209Y. Then, the photoreceptor drum 209Y is on standby for subsequent image formation.

The yellow toner image formed on the conveyance belt 205 by the image forming unit 206Y is then transported to the image forming unit 206M as the conveyance belt 205 is rotated by the rollers. The image forming unit 206M performs image forming processes similar to those performed by the image forming unit 206Y, thereby forming a magenta toner image on the photoreceptor drums 209M, and the magenta toner image is transferred and superimposed on the yellow toner image.

The yellow and magenta toner images on the conveyance belt 205 are further transported to the image forming units 206C and 206K, where cyan and black toner images are formed on the photoreceptor drums 209C and 209K, respectively, and the cyan and black toner images are transferred on the superimposed toner image on the conveyance belt 205. Thus, a multicolor intermediate toner image is formed on the conveyance belt 205.

The sheets 204 contained in the sheet tray 201 are sent out from the top sequentially. At a position where a conveyance channel leading therefrom contacts or is closest to the conveyance belt 205, the intermediate toner image is transferred from the conveyance belt 205 onto the sheet 204. Thus, an image is formed on the sheet 204. The sheet 204 carrying the image is transported to a fixing device 216, where the image is fixed on the sheet 204. Then, the sheet 204 is discharged outside the image forming apparatus 200.

The conveyance belt 205 is provided with a belt cleaner 218. The belt cleaner 218 can include a cleaning blade pressed against the conveyance belt 205 to scrape off toner from the surface of the conveyance belt 205 at a position downstream from the secondary-transfer position and upstream from the photoreceptor drums 209 in the direction in which the conveyance belt 205 rotates (in the direction indicated by arrows indicating the direction of rotation of the driving roller 207 and the driven roller 208) as shown in FIG. 14. Thus, the belt cleaner 218 serves as a toner remover.

The image forming apparatus 200 having the above-described configuration is controlled by the controller 1 shown in FIG. 1. The magnetic permeability sensor 100 according to the first embodiment is provided to the developing device 212 among the components shown in FIG. 14.

Next, descriptions are given below of the developing device 212 according to the present embodiment with reference to FIGS. 15 and 20.

Figure 15:
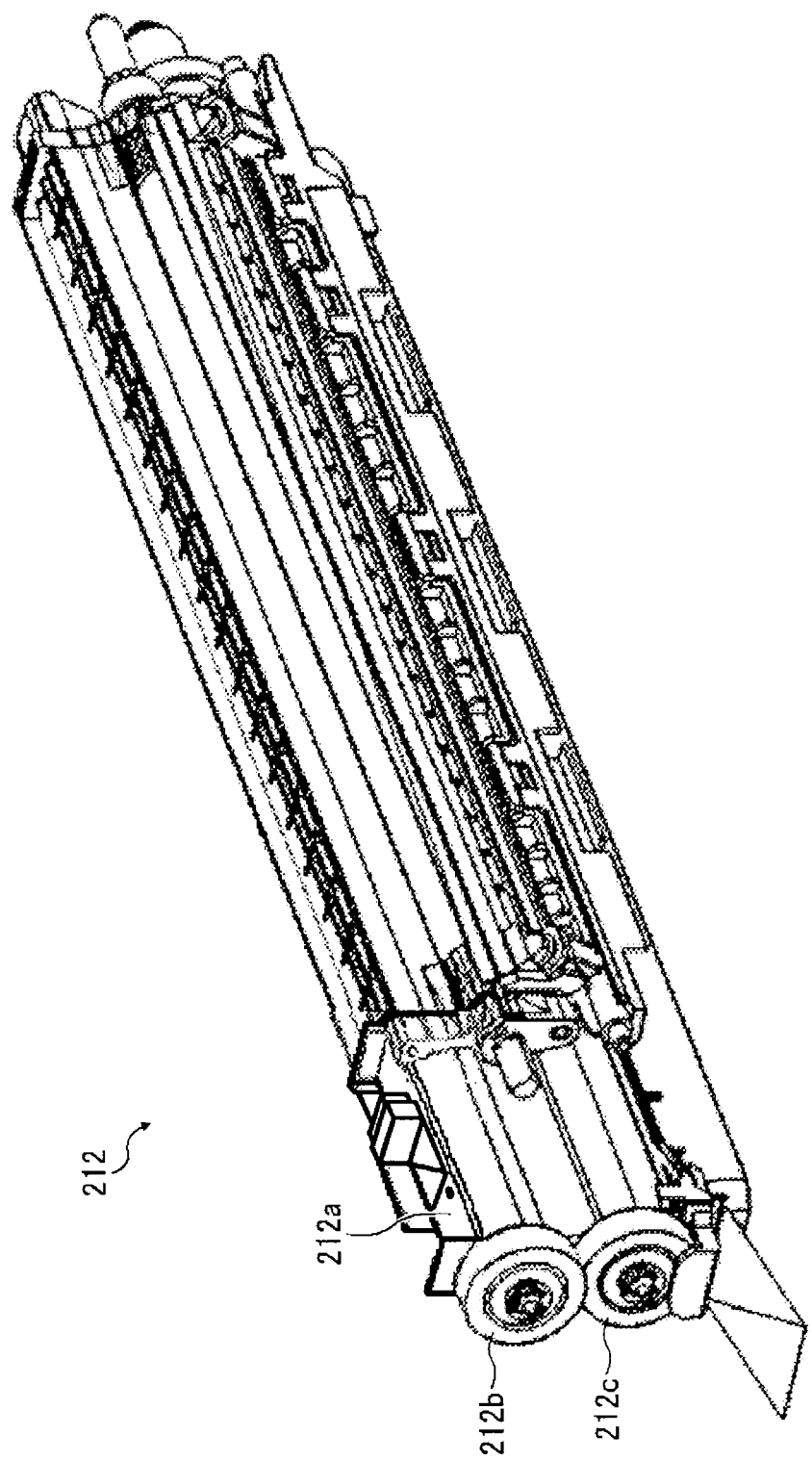
FIG. 15 is a perspective view illustrating the developing device according to the second embodiment, provided with the magnetic permeability sensor shown in FIG. 3.

FIG. 15 is a perspective view that illustrates an exterior of the developing device 212. It is to be noted that, in FIG. 15, the developing device 212 is placed upside down from the posture mounted in the image forming apparatus 200, that is, from the posture of the developing device 212 being used. FIG. 20 is a perspective view illustrating an interior of the developing device 212 according to the present embodiment. It is to be noted that the developing device 212 shown in FIG. 20 is upside down from that in FIG. 15. Accordingly, FIG. 20 illustrates the posture of the developing device 212 in the image forming apparatus 200, that is, the developing device 212 being used.

Figure 20:
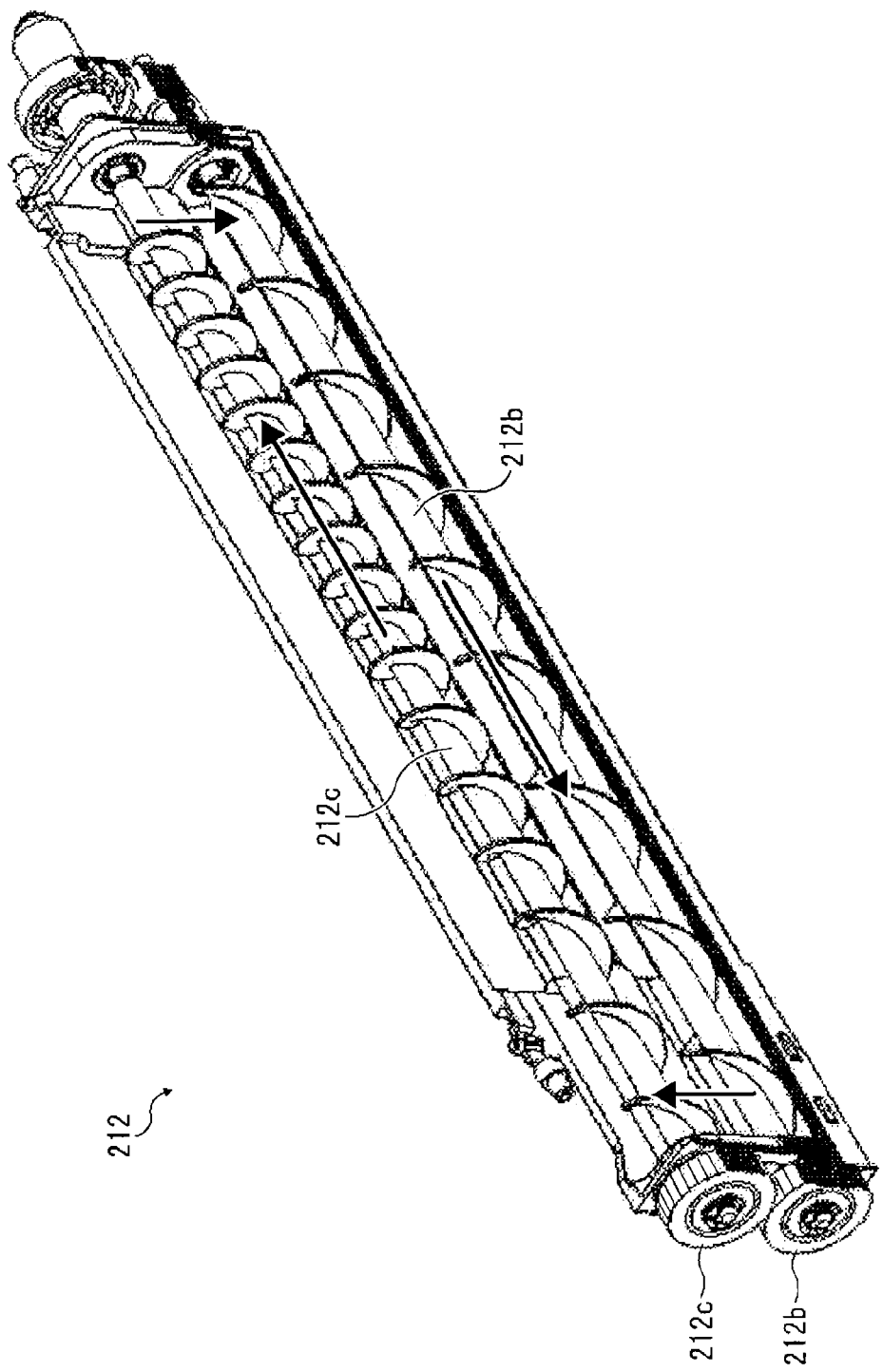
FIG. 20 is a perspective view illustrating an interior of the developing device.

Additionally, the longitudinal direction of the developing device 212 shown in FIGS. 15 and 20 is perpendicular to the surface of the paper on which FIG. 14 is drawn. That is, the longitudinal direction of the developing device 212 in FIGS. 15 and 20 parallels the surface of the conveyance belt 205 and perpendicular to the belt conveyance direction. As shown in FIGS. 15 and 20, inside the developing device 212, conveying screws 212b and 212c are provided to transport developer contained therein. As the conveying screws 212b and 212c rotate in the opposite directions, developer is distributed in the entire developing device 212 in the longitudinal direction thereof. In other words, the entire interior of the developing device 212 is used as the developer container.

As shown in FIG. 20, at the longitudinal end of the developing device 212, developer transported therein is forwarded from a conveyance channel in which the conveying screw 212b transports developer to a conveyance channel in which developer is transported by the conveying screw 212c. Accordingly, developer is densest in end portions in the longitudinal direction of the developing device 212 that serve as developer transit portions, through which developer moves from one conveyance channel to the other conveyance channel. The magnetic permeability sensor 100 according to the present embodiment is attached to the sensor mounting portion 212a shown in FIG. 15 to detect the density of developer (density of toner included in developer) in the developer transit portion. Thus, the magnetic permeability sensor 100 is used as a developer density detector.

The magnetic permeability sensor 100 is attached to the sensor mounting portion 212a opposed to the developer transit portion because the amount by which magnetic permeability changes increases as developer becomes denser. Therefore, disposing the magnetic permeability sensor 100 at the position opposed to the developer transit portion, where developer is densest, can make detection of magnetic permeability inside the developing device 212 more preferable.

It is to be noted that, although the amount of changes in the magnetic permeability differs, magnetic permeability arises in any portion where developer is present. Therefore, disposing the magnetic permeability sensor 100 at the sensor mounting portion 212a is not a requisite for the detection. In the magnetic permeability sensor 100, upon application of power supply voltage, electrical current (hereinafter simply "current") flows through the coil pattern 101. The current causes a magnetic flux in a predetermined direction, and the magnetic permeability sensor 100 outputs from the output terminal 108 a signal at a frequency corresponding to the magnetic permeability in the range of action of the magnetic flux. Accordingly, the magnetic permeability sensor 100 can detect the magnetic permeability as long as the magnetic permeability sensor 100 is disposed such that the magnetic flux of the coil pattern 101 can acts in the space where developer is contained.

Figure 16:
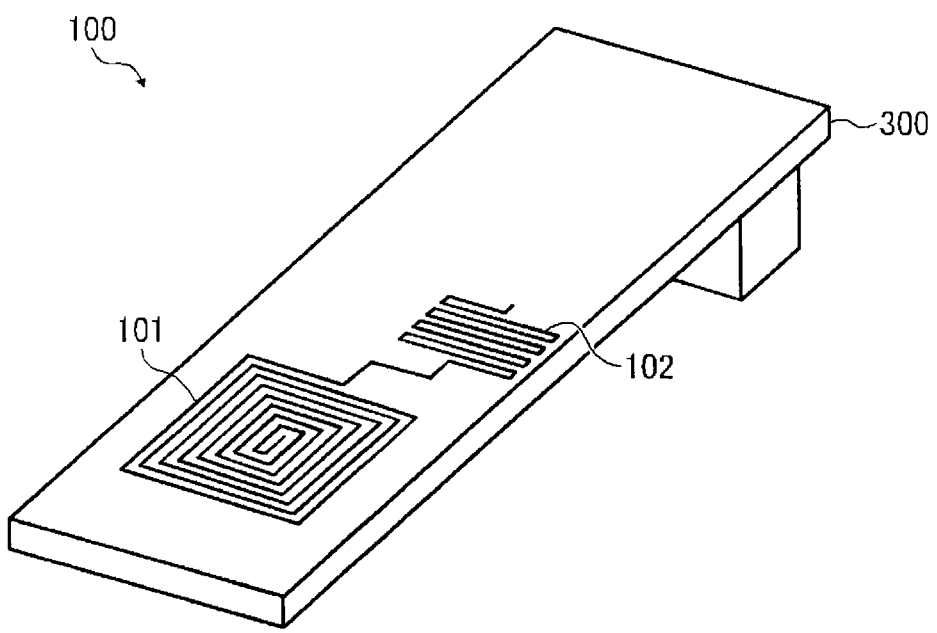
FIG. 16 is a perspective view illustrating an exterior of the magnetic permeability sensor according to the second embodiment.

Next, descriptions are given below of external configuration of the magnetic permeability sensor 100 according to the present embodiment. FIG. 16 is a perspective view illustrating an exterior of the magnetic permeability sensor 100 according to the present embodiment. In FIG. 16, the detection face, that is, the first face on which the coil pattern 101 and the planar adjusting resistor 102 are provided, is faced up. The detection face is to oppose to the space subjected to magnetic permeability detection.

As shown in FIG. 16, the adjusting resistor 102, which is connected serially to the coil pattern 101, is printed on the detection face on which the coil pattern 101 is printed. As described above with reference to FIG. 3, the coil pattern 101 is constructed of conducting wire (signal line) printed in a spiral shape on the detection face. The adjusting resistor 102 is constructed of conducting wire (signal line) printed in a serpentine shape on the detection face. The coil and resistor patterns realize the above-described functions of the magnetic permeability sensor 100 and, simultaneously, decorates the appearance as shown in FIG. 16.

The coil pattern 101 serves as the detecting portion of the magnetic permeability sensor 100 to detect magnetic permeability. The magnetic permeability sensor 100 is attached to the developing device 212 with the detecting portion opposed to the above-described developer transit portion. In other words, the magnetic permeability sensor 100 is attached to the developing device 212 so that the magnetic permeability sensor 100 generates a magnetic flux toward the developer transit portion and the developer transit portion at least partly occupies the range of action of the magnetic flux.

Figure 17A:
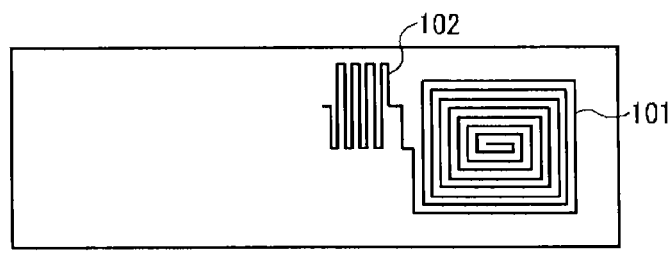
FIG. 17A through 17F illustrate six sides of the magnetic permeability sensor shown in FIG. 16.
Figure 17B:
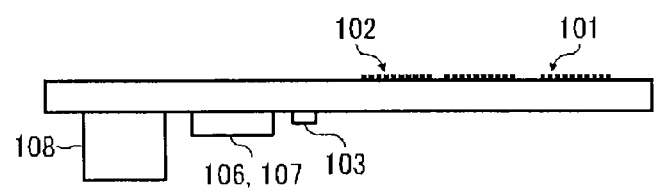
Figure 17C:
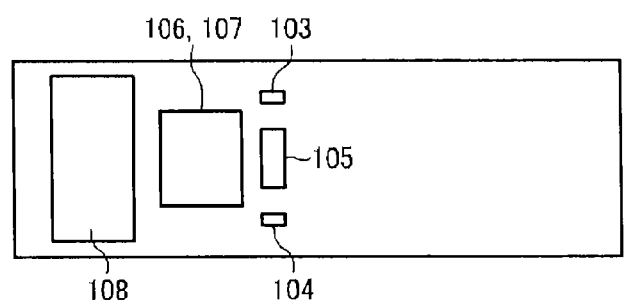
Figure 17D:
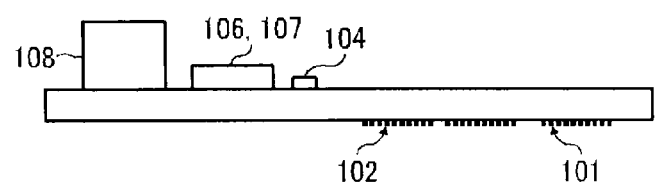
Figure 17E:
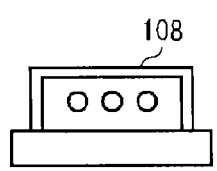
Figure 17F:
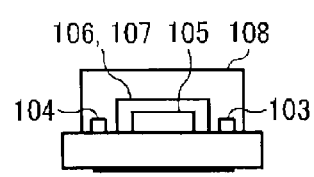

FIGS. 17A through 17F constitute a set of six side-views of the magnetic permeability sensor 100. As shown in FIGS. 17B, 17C, and 17D, the first and second capacitors 103 and 104, the feedback resistor 105, the unbuffered ICs 106 and 107, and the output terminal 108 are disposed on the second face of the board 300 constituting the magnetic permeability sensor 100, opposite the first face (detection face) on which the coil pattern 101 and the adjusting resistor 102 are disposed.

With this arrangement, surface unevenness of the first face attached to the developing device 212 can be substantially eliminated. Accordingly, the magnetic permeability sensor 100 can be disposed so that the detection face provided with the coil pattern 101 having sensing capabilities can oppose to the developer transit portion, which is the magnetic permeability detection target, with the detection face in contact with the developing device 212.

Additionally, on the second face (back face) of the magnetic permeability sensor 100, neither electronic components nor conducting wire is disposed in an area that overlaps with the area occupied by the coil pattern 101. This arrangement can inhibit another electronic component or conducting wire from affecting the magnetic permeability detection by the coil pattern 101, thus enhancing the accuracy of magnetic permeability detection.

Next, descriptions are given below of attachment of the magnetic permeability sensor 100 to the developing device 212 with reference to FIG. 18.

Figure 18:
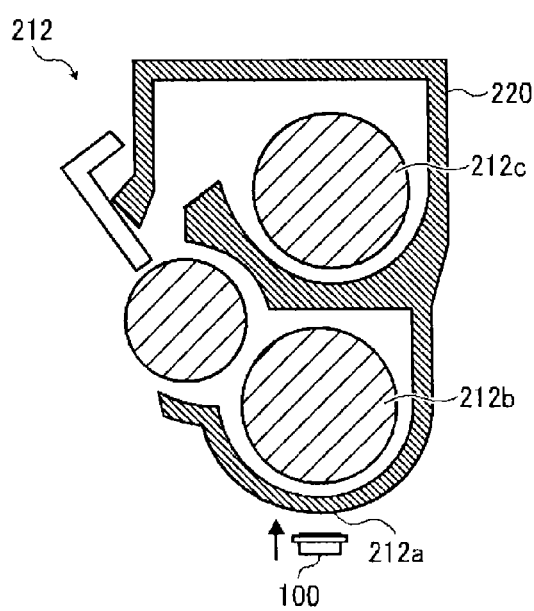
FIG. 18 is a cross-sectional view illustrating location of the magnetic permeability sensor provided to the developing device according to the second embodiment.

FIG. 18 illustrates a position of the magnetic permeability sensor 100 provided to the developing device 212. In FIG. 18, a cross section as viewed from a side of the developing device 212 is illustrated, and the developing device 212 is upside down from the posture shown in the perspective view in FIG. 15. That is, the upper and lower sides in FIG. 18 correspond to those in FIG. 20. Accordingly, FIG. 18 illustrates the posture of the developing device 212 in the image forming apparatus 200, that is, the developing device 212 being used.

Referring to FIG. 18, the conveying screws 212b and 212c are disposed inside a casing 220 of the developing device 212 and transport developer in the longitudinal direction of the developing device 212.

The sensor mounting portion 212a is planar to facilitate attachment of the magnetic permeability sensor 100, which is based on a planar board. The magnetic permeability sensor 100 is attached to the developing device 212 with the detection face thereof facing the planar sensor mounting portion 212a. As shown in FIG. 18, the casing of the developing device 212 is shaped to conform to the shapes of the conveying screws 212b and 212c, and a portion including the sensor mounting portion 212a is arcuate in cross section to conform to the circular cross-sectional shape of the conveying screw 212b.

Since a part of the arcuate casing is made planar into the sensor mounting portion 212a, the distance from the coil pattern 101 of the magnetic permeability sensor 100 attached to the sensor mounting portion 212a to the developer transit portion inside the developing device 212 is reduced, and the range of action of the magnetic flux can be directed toward the developer transit portion. With this configuration, the magnetic permeability sensor 100 attached to the sensor mounting portion 212a can detect the density of developer (magnetic permeability) inside the developer transit portion more preferably.

Generally, developer used in electrophotographic image forming apparatuses having such a configuration is a mixture of toner and carrier. To develop electrostatic latent images formed on the photoreceptor drum 209, the density of toner included in developer is kept at a predetermined value or higher. Since the density of toner changes as the electrostatic latent images are developed, it is necessary to detect the density of toner inside the developing device 212. In the present embodiment, as the density of toner inside the developing device 212 changes, the magnetic permeability inside the range of action of the magnetic flux exerted by the coil pattern 101 changes. The density of toner included in developer in the developing device 212 can be detected by detecting the change by the magnetic permeability sensor 100.

Thus, according to the present embodiment, the density of toner inside the developing device 212 can be detected by the magnetic permeability sensor 100.

[Variations]

The description above concerns the magnetic permeability sensor 100 that detects the magnetic permeability in the range of action of the magnetic flux using the planer coil pattern 101. By contrast, assuming that the magnetic permeability in the range of action of the magnetic flux exerted by the coil pattern 101 is constant, it can be deemed that fluctuations in the oscillation frequency of the circuit shown in FIG. 3 is caused by temperature change described with reference to FIGS. 12A through 12D.

Accordingly, the above-described magnetic permeability sensor 100 can be used as a temperature detector as well. In this case, the temperature characteristics described with reference to FIGS. 12A through 12D preferably have a tendency of simple rise or simple descent in the range of detection temperature. With this configuration, temperature of the portion where the sensor is mounted can be detected with simple calculation based on the oscillation frequency. From this point of view as well, it is useful when the temperature characteristics of the oscillation frequency of the circuit are adjustable by adjusting the adjusting resistor 102 that is a planar resistor to adjust the resistance.

Third Embodiment

A third embodiment described below concerns protection of a planar coil and a planar, serpentine) resistor provided on a board, in a magnetic permeability sensor employing an LC oscillator circuit including the planar coil and the planar, resistor. It is to be noted that, the third embodiment is described using as an example a case in which the magnetic permeability sensor is provided to a developing device of an electrophotographic image forming apparatus using two-component developer including magnetic carrier particles and toner particles (i.e., nonmagnetic developer) and used as a toner density detector to detect the density of toner of the two-component developer inside the developing device.

As described in the second embodiment above, image forming apparatuses using two-component developer typically include a toner density detector to detect the density of toner inside a container. Toner density detectors employing the above-described LC oscillator circuit including the coil detect the magnetic permeability inside the container opposed to the coil formation face, based on the frequency of signals output from the LC oscillator circuit, thereby detecting the density of toner inside the container. In other words, the toner density detector employing the LC oscillator circuit including the coil detects, via changes in inductance of the coil, changes in the magnetic permeability resulting from changes in the density of toner inside the container due to the consumption of toner in image formation.

Accordingly, it is required that the coil formation face is attached to a portion opposed to the container to enable the toner density detector employing the LC oscillator circuit including the coil to exert its capability.

In repair and reuse of the above-described toner density detector, generally tapered tools such as precision screwdrivers and slotted screwdrivers are used. Users or operators insert the end of the tapered tool into clearance between a mounting face of the container and the toner density detector to remove the toner density detector from the container.

This removal work demands care not to damage the coil with the tool such as precision screwdrivers. Since the toner density detector detects the density of toner inside the container via the inductance of the coil, the density of toner is not accurately detected if the coil is damaged.

However, the toner density detector is attached to the container with the coil formation face opposed to the container as described above, and it is difficult for the operator to accurately recognize the position of the coil. Accordingly, there is a risk that the operator unintentionally damages the coil during the removal work.

Additionally, after manufacturing, the toner density detector is stored or transported independently with the coil exposed, and there is the risk of damage to the coil also at that time.

It is to be noted that the above-described risk arises, not only in the toner density detector, also in other magnetic permeability detectors that include an LC oscillator circuit including a coil constructed of a planar pattern provided on a board to detect magnetic permeability inside a predetermined space opposed to the coil formation face, based on the frequency of signals output from the LC oscillator circuit in response to the magnetic permeability inside the predetermined space.

In view of the foregoing, descriptions are given below of configurations to protect the coil in such magnetic permeability detectors.

Attachment of a magnetic permeability sensor to the developing device 212 according to the present embodiment is described below with reference to FIGS. 21 through 24. It is to be noted that the magnetic permeability sensor 100 according to the first embodiment can be used preferably in the present embodiment.

Figure 21:
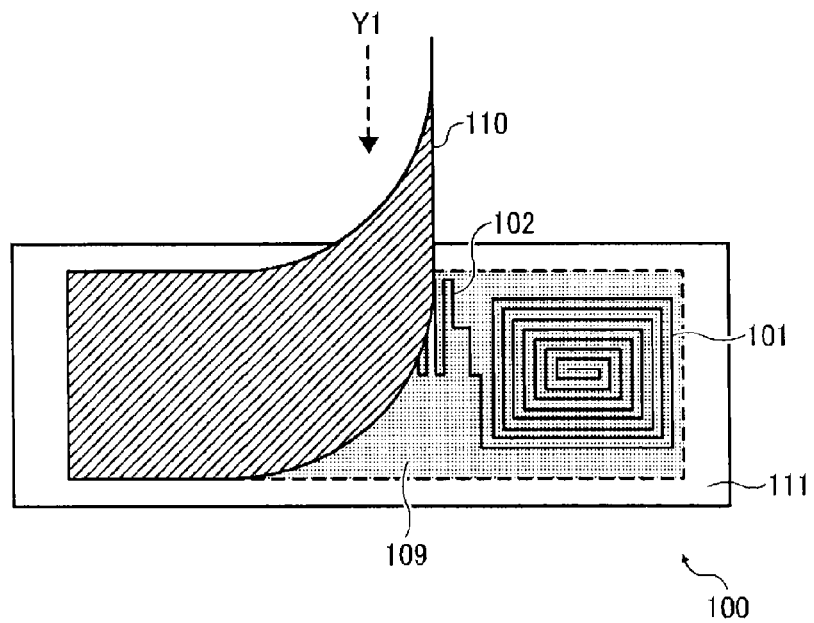
FIG. 21 illustrates the magnetic permeability sensor according to a third embodiment from a detection face thereof.
Figure 22:
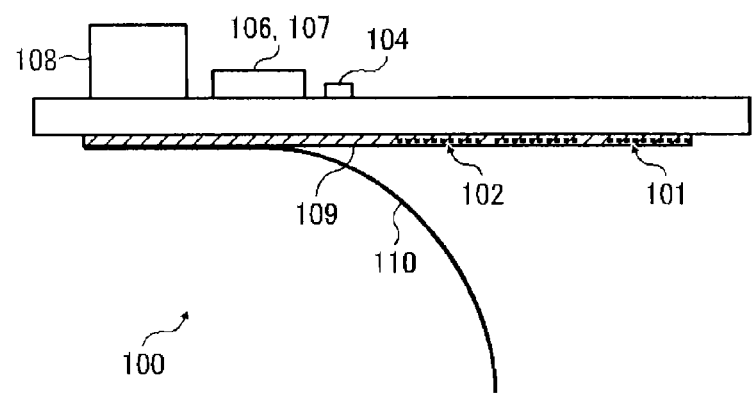
FIG. 22 illustrates the magnetic permeability sensor shown in FIG. 21, as viewed in a direction horizontal to the detection face and perpendicular to the direction in which the coil pattern and the resistance pattern are connected to each other.

FIG. 21 illustrates the magnetic permeability sensor 100 from the detection face thereof. FIG. 22 illustrates the magnetic permeability sensor 100 as viewed in a direction horizontal to the detection face and perpendicular to the direction in which the coil pattern 101 and the adjusting resistor 102 are serially connected. That is, FIG. 22 illustrates the magnetic permeability sensor 100 as viewed in the direction indicated by arrow Y1 shown in FIG. 21.

Figure 23:
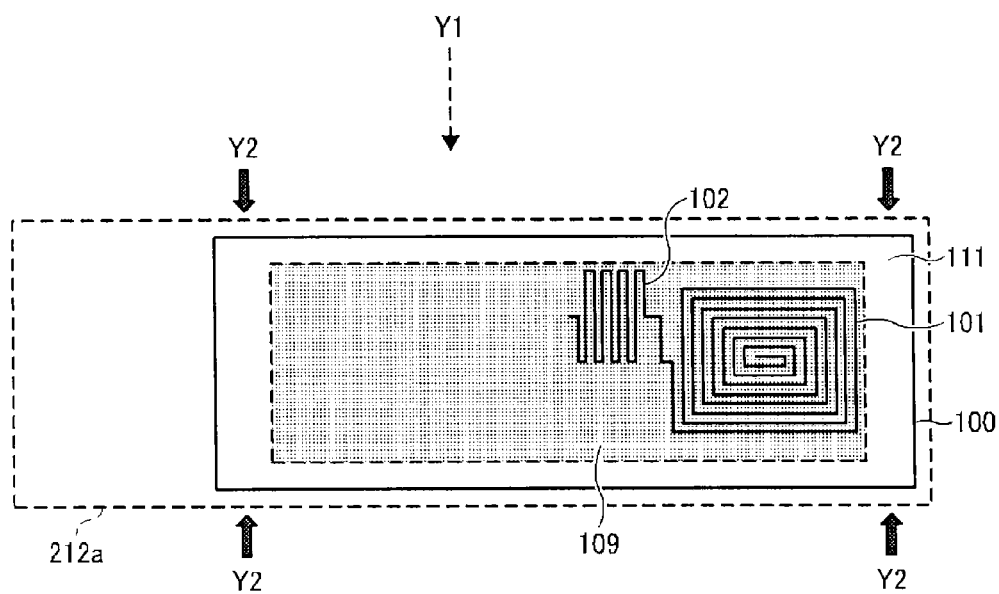
FIG. 23 illustrates the magnetic permeability sensor according to the third embodiment, being attached to the developing device, as viewed from the detection face thereof.
Figure 24:
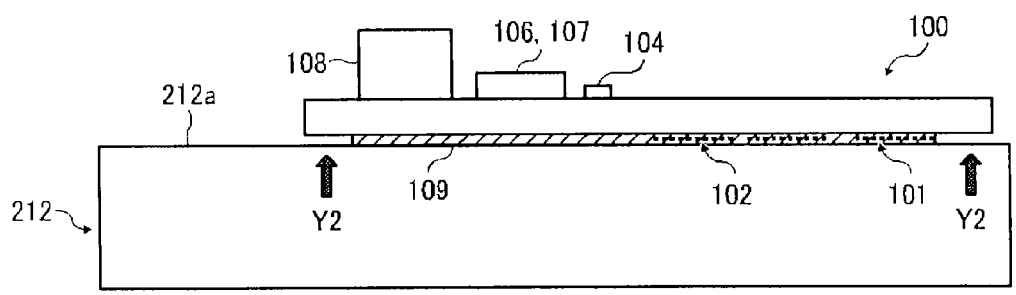
FIG. 24 illustrates the magnetic permeability sensor according to the third embodiment, being attached to the developing device and viewed in the direction horizontal to the detection face and perpendicular to the direction in which the resistance pattern is connected to the coil pattern.

FIG. 23 illustrates the magnetic permeability sensor 100 as viewed from the detection face thereof in a state in which the magnetic permeability sensor 100 is attached to the developing device 212. FIG. 24 illustrates the magnetic permeability sensor 100 being attached to the developing device 212, as viewed in the direction horizontal to the detection face and perpendicular to the direction of serial connection of the coil pattern 101 and the adjusting resistor 102. That is, FIG. 24 illustrates the magnetic permeability sensor 100 as viewed in the direction indicated by arrow Y1 shown in FIG. 23.

As shown in FIGS. 21 and 22, the magnetic permeability sensor 100 according to the present embodiment includes an adhesive layer 109 extending over the detection face substantially entirely, but a clearance 111 is left around the adhesive layer 109. The adhesive layer 109 can be formed of double-sided adhesive tape, glue, or the like. Additionally, an adhesive face of the adhesive layer 109 is covered with film 110, such as cellophane or the like, as shown in FIGS. 21 and 22.

In attachment of the magnetic permeability sensor 100 to the developing device 212, the operator initially removes the film 110 from the adhesive face of the adhesive layer 109. Subsequently, as shown in FIGS. 23 and 24, the operator presses the exposed adhesive face of the adhesive layer 109 against the sensor mounting portion 212a of the developing device 212. Then, the magnetic permeability sensor 100 is attached to the sensor mounting portion 212a with adhesion force of the adhesive layer 109. Thus, according to the present embodiment, the operator can attach the magnetic permeability sensor 100 to the developing device 212 easily.

It is to be noted that a face of the adhesive layer 109 on the side of the sensor mounting portion 212a is referred to as a first face (i.e., a mount side), and the opposite face of the adhesive layer 109, which is bonded to the magnetic permeability sensor 100, is referred to as second face (i.e., a sensor side).

Further, as described above, the adhesive layer 109 is provided to the substantially entire area of the detection face of the magnetic permeability sensor 100, and the film 110 covers the adhesive layer 109. Therefore, according to the present embodiment, the coil pattern 101 and the adjusting resistor 102 can be protected during storage and transport of the magnetic permeability sensor 100.

Next, removal of the magnetic permeability sensor 100 is described with reference to FIGS. 23 and 24. As described above, the magnetic permeability sensor 100 is attached to the sensor mounting portion 212a with adhesion force of the first face of the adhesive layer 109.

To remove the magnetic permeability sensor 100 from the developing device 212 for repair or reuse, the operator initially inserts an end of a removal tool into the clearance 111 at the positions indicated by arrows Y2 in FIGS. 23 and 24, that is, at corners of the magnetic permeability sensor 100, between the detection face of the magnetic permeability sensor 100 and the sensor mounting portion 212a. By the thickness of the adhesive layer 109 between the detection face of the magnetic permeability sensor 100 and the sensor mounting portion 212a, the clearance 111 is present adjacent to the adhesive layer 109. The clearance 111 serve as guides for guiding the removal tool used by the operator. It is to be noted that the removal tool in the present embodiment can be a tapered tool such as a precision screwdriver, a slotted screwdriver, and the like.

Inserting the end of the removal tool, the operator removes the magnetic permeability sensor 100 from the sensor mounting portion 212a using the principle of leverage. Thus, according to the present embodiment, the operator can remove the magnetic permeability sensor 100 from the developing device 212 easily.

Additionally, the clearances at the corners created by the thickness of the adhesive layer 109 between the detection face of the magnetic permeability sensor 100 and the sensor mounting portion 212a can serve as the guides as described above. Accordingly, even if the operator does not accurately recognize the positions of the coil pattern 101 and the adjusting resistor 102, the operator can avoid the coil pattern 101 and the adjusting resistor 102, guided by the clearance, when inserting the end of the removal tool. Therefore, this configuration can reduce the risk of damaging the coil pattern 101 and the adjusting resistor 102 with the removal tool during removal. Thus, according to the present embodiment, the coil pattern 101 and the adjusting resistor 102 can be protected during removal of the magnetic permeability sensor 100.

Further, if the operator incidentally inserts the removal tool directly into the area to which the adhesive layer 109 is bonded, not via the clearance, the elastic force or adhesion force of the adhesive layer 109 can prevent the end of the tool from reaching the coil pattern 101 and the adjusting resistor 102. Therefore, even in such events, this configuration can eliminate or reduce the risk that the operator unintentionally damages the coil pattern 101 and the adjusting resistor 102 with the removal tool during removal. Thus, according to the present embodiment, even if the operator unintentionally inserts the removal tool into not the clearance but directly the area to which the adhesive layer 109 is bonded during removal of the magnetic permeability sensor 100, the coil pattern 101 and the adjusting resistor 102 can be protected.

It is to be noted that, although the description above concerns the configuration in which the magnetic permeability sensor 100 is attached to the sensor mounting portion 212a due to the adhesion force exerted by the adhesive layer 109 extending over the substantially entire area of the detection face, the adhesive layer 109 may be configured otherwise as shown in FIGS. 25 through 28.

Figure 25:
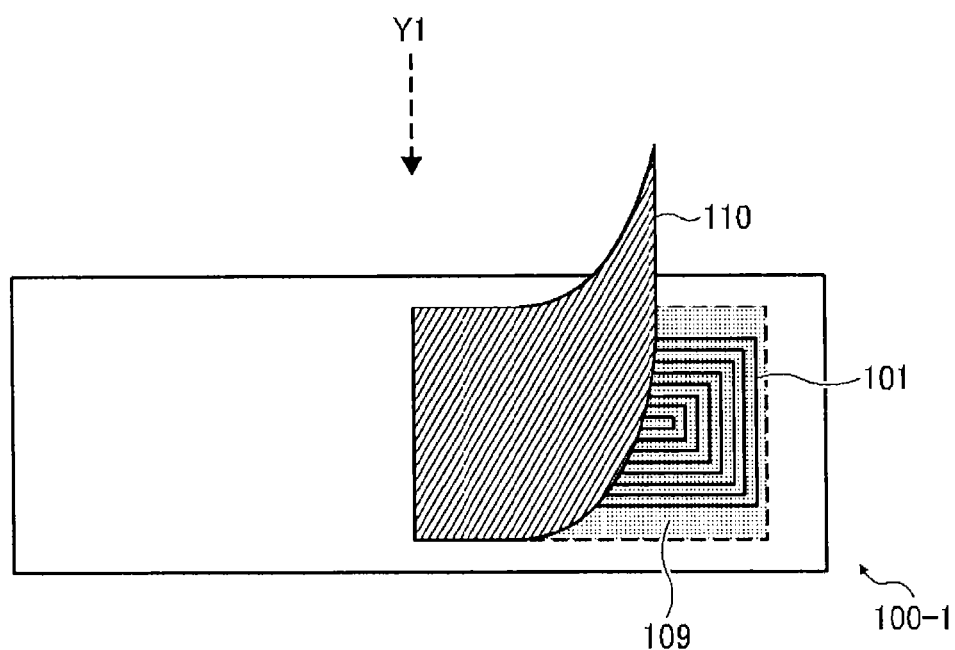
FIG. 25 illustrates a magnetic permeability sensor according to a variation, as viewed from a detection face thereof.
Figure 26:
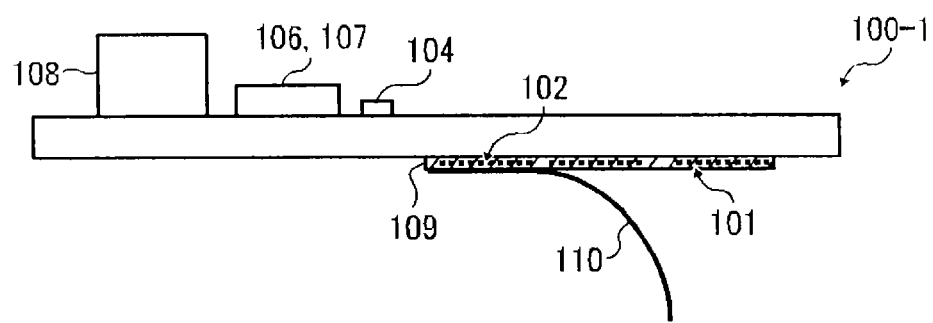
FIG. 26 illustrates the magnetic permeability sensor shown in FIG. 25, as viewed in the direction horizontal to the detection face and perpendicular to the direction in which the resistance pattern is connected to the pattern coil.
Figure 27:
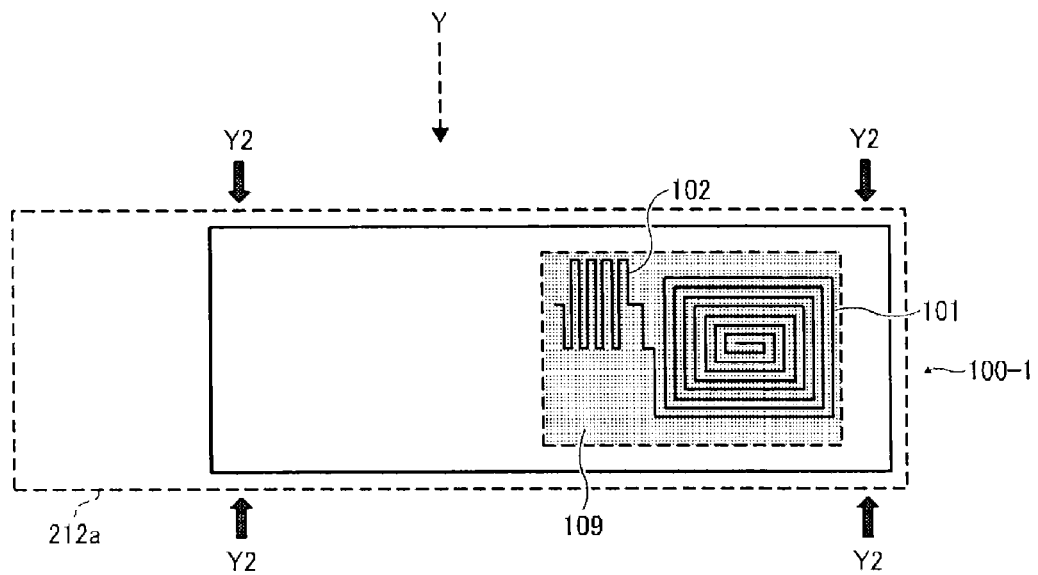
FIG. 27 illustrates the magnetic permeability sensor shown in FIG. 25, as viewed from the detection face thereof in a state in which the magnetic permeability sensor is attached to the developing device.
Figure 28:
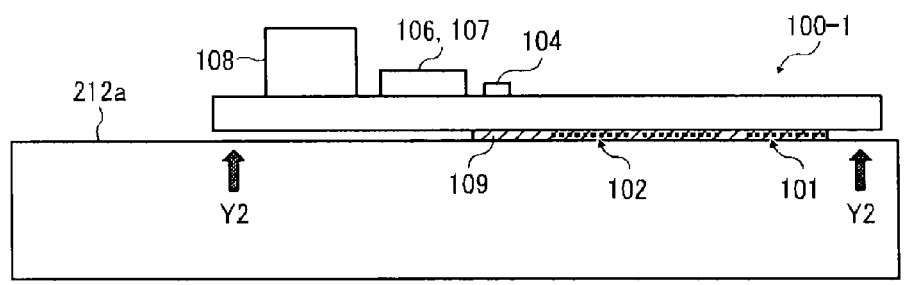
FIG. 28 illustrates the magnetic permeability sensor shown in FIG. 25, being attached to the developing device and viewed in the direction horizontal to the detection face and perpendicular to the direction in which the resistance pattern is connected to the coil pattern.
Figure 29:
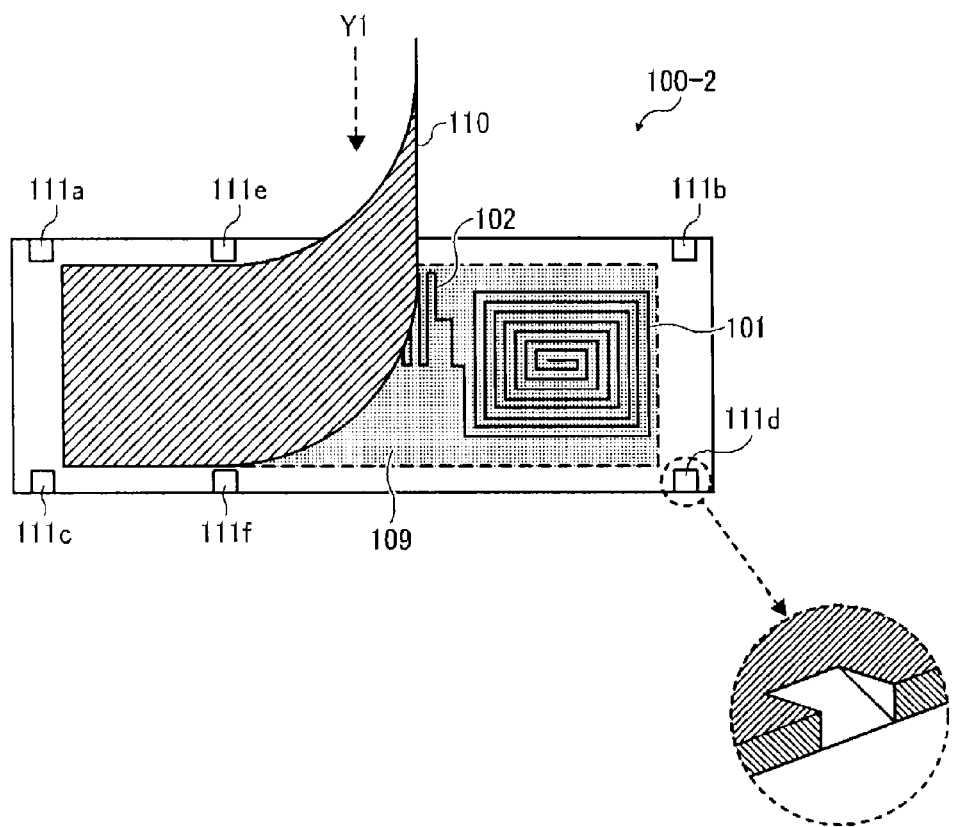
FIG. 29 illustrates the magnetic permeability sensor according to another variation as viewed from a detection face thereof.
Figure 30:
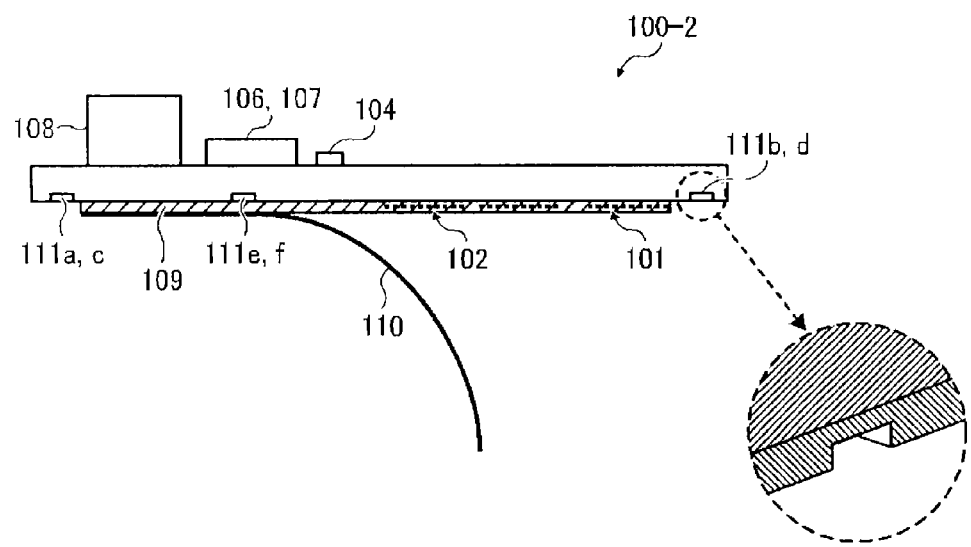
FIG. 30 illustrates the magnetic permeability sensor shown in FIG. 29, as viewed in a direction horizontal to the detection face and perpendicular to the direction in which the resistance pattern is connected to the coil pattern.
Figure 31:
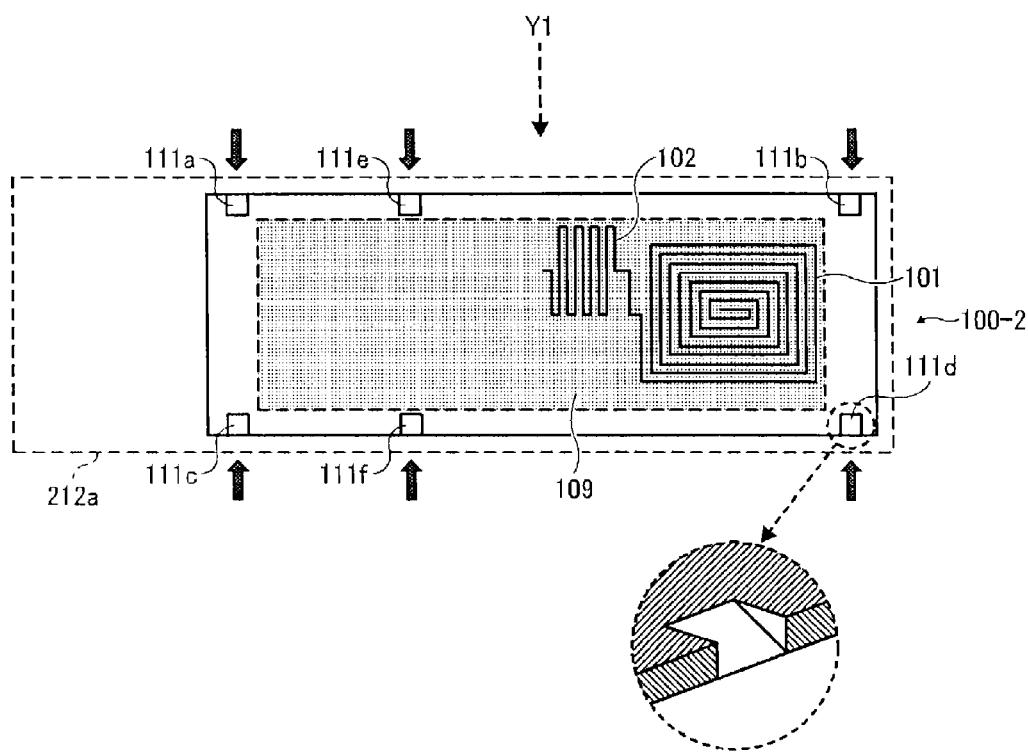
FIG. 31 illustrates the magnetic permeability sensor shown in FIG. 29, being attached to the developing device, as viewed from the detection face thereof.
Figure 32:
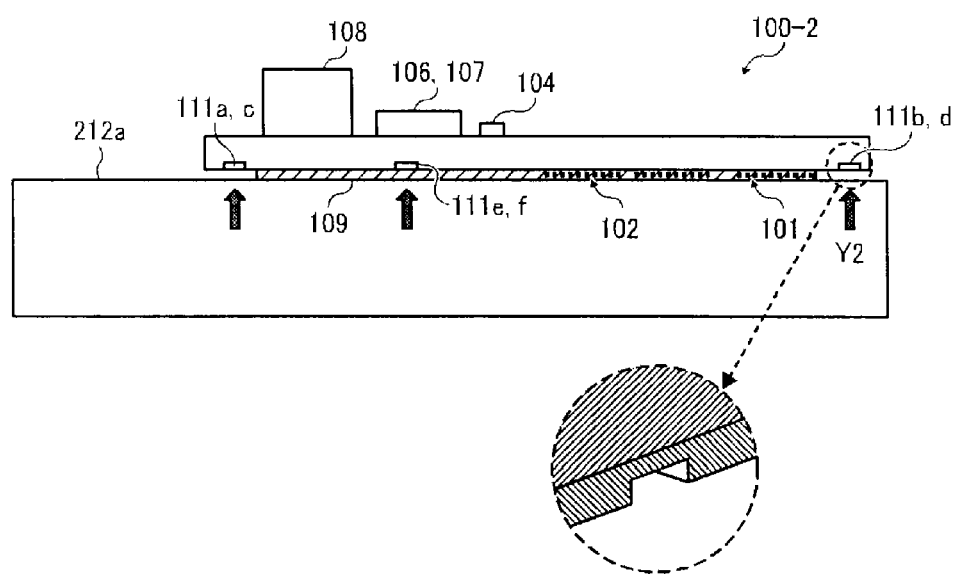
FIG. 32 illustrates the magnetic permeability sensor shown in FIG. 29, being attached to the developing device and viewed in the direction horizontal to the detection face and perpendicular to the direction in which the resistance pattern is connected to the coil pattern.

FIGS. 25 and 27 illustrate the magnetic permeability sensor 100-1 as viewed from the detection face thereof, respectively not attached and being attached to the developing device 212. FIGS. 26 and 28 illustrate the magnetic permeability sensor 100-1 as viewed in the direction horizontal to the detection face and perpendicular to the direction of serial connection of the coil pattern 101 and the adjusting resistor 102, respectively not attached and being attached to the developing device 212. That is, FIGS. 26 and 28 illustrate the magnetic permeability sensor 100-1 as viewed in the direction indicated by arrow Y1 shown in FIGS. 25 and 27, respectively.

As shown in FIGS. 25 through 28, in the magnetic permeability sensor 100-1, the adhesive layer 109 may occupy not the substantially entire area of the detection face but only an area in which the coil pattern 101 and the adjusting resistor 102 are present so that the magnetic permeability sensor 100-1 is attached to the sensor mounting portion 212a due to the adhesion force exerted by the adhesive layer 109.

The configuration shown in FIGS. 25 through 28 can attain effects similar to those attained by the configuration shown in FIGS. 21 through 24 and is advantageous in that the manufacturing cost is reduced. Covering the area in which the coil pattern 101 and the adjusting resistor 102 are present with the adhesive layer 109 is sufficient for attaining the effects of the present embodiment, that is, eliminating or reducing the risk that the operator unintentionally damages the coil pattern 101 and the adjusting resistor 102 with the tool during the removal.

Further, relative adhesion strength of the first and second faces of the adhesive layer 109 is described. In the configurations described above with reference FIGS. 23, 24, 27, and 28, the magnetic permeability sensor 100 or 100-1 (hereinafter collectively "magnetic permeability sensor 100") is attached to the sensor mounting portion 212a using the adhesion of the adhesive layer 109. At that time, an inconvenience may arise if the strength of adhesion exerted on the first face of the adhesive layer 109 and the sensor mounting portion 212a bonded to each other is similar or greater than the strength of adhesion between the second face of the adhesive layer 109 and the magnetic permeability sensor 100. That is, in removal of the magnetic permeability sensor 100 from the sensor mounting portion 212a, it is difficult to separate the first face of the adhesive layer 109 from the sensor mounting portion 212a, whereas the second face of the adhesive layer 109 is separated from the magnetic permeability sensor 100 more easily.

When the adhesive layer 109 comes off the magnetic permeability sensor 100, it is possible that the coil pattern 101 and the adjusting resistor 102 are damaged by the adhesion force. This inconvenience can be eliminated by keeping the strength of the adhesion between the first face of the adhesive layer 109 and the sensor mounting portion 212a smaller than the strength of the adhesion between second face of the adhesive layer 109 and the magnetic permeability sensor 100, by for example, embossing, texturing (grain finishing), or frosting of the surface of the sensor mounting portion 212a.

Alternatively, the adhesive layer 109 may be constructed of a material having front and back sides different in the strength of adhesion. In this case, the stronger adhesion side is bonded to the detection face of the magnetic permeability sensor 100, and the weaker adhesion side is bonded to the sensor mounting portion 212a. Additionally, the adhesive layer 109 may be constructed of a material that changes in adhesion force depending on the material of the face to which the adhesive layer 109 is bonded, and the material of the adhesive layer 109 may be selected considering the material of the detection face of the magnetic permeability sensor 100 and that of the surface of the sensor mounting portion 212a.

Fourth Embodiment

As described above with reference FIGS. 23, 24, 27, and 28, in the third embodiment, the clearances serving as the guide for guiding the removal tool is created when the magnetic permeability sensor 100 is attached to the sensor mounting portion 212a using the adhesion of the adhesive layer 109.

Accordingly, even if the operator does not accurately recognize the positions of the coil pattern 101 and the adjusting resistor 102, the removal tool used by the operator can be guided away the coil pattern 101 and the adjusting resistor 102. Therefore, this configuration can reduce the risk of damaging the coil pattern 101 and the adjusting resistor 102 with the removal tool.

By contrast, in a magnetic permeability sensor 100-2 according to the fourth embodiment, chamfered or recessed portions are provided at or adjacent to corners of the detection face, thereby providing the guide portions to guide the operator not to reach the area where the coil pattern 101 and the adjusting resistor 102 are present in removal of the magnetic permeability sensor 100-2.

In this case, even if the operator does not accurately recognize the positions of the coil pattern 101 and the adjusting resistor 102, the removal tool used by the operator can be guided not to reach these elements more reliably.

Therefore, this configuration can secure prevention of damage to these elements with the removal tool and protection thereof during the removal of the magnetic permeability sensor 100-2.

Descriptions are given in further detail below. It is to be noted that elements in the fourth embodiment similar to those of the third embodiment are given identical or similar reference characters, and thus descriptions thereof omitted.

FIGS. 29 through 32 illustrate the magnetic permeability sensor 100-2 according to the fourth embodiment. FIGS. 29 through 32 respectively correspond to FIGS. 21 through 24 illustrating the magnetic permeability sensor 100 according to the third embodiment.

As shown in FIGS. 29 through 32, in the magnetic permeability sensor 100-2 according to the present embodiment, guide portions 111a through 111f, which are chamfered or recessed, are provided at or adjacent to corners of an area where the adhesive layer 109 is not provided or an area where the coil pattern 101 and the adjusting resistor 102 are not present. This configuration can reliably guide the operator to the area free from the coil pattern 101 and the adjusting resistor 102 during the removal of the magnetic permeability sensor 100-2.

Accordingly, even if the operator does not accurately recognize the positions of the coil pattern 101 and the adjusting resistor 102, the operator can avoid these elements more reliably in inserting the removal tool. Therefore, this configuration can secure prevention of damage to these elements by the removal tool and protection thereof during the removal of the magnetic permeability sensor 100-2.

It is to be noted that the positions of the guide portions 111a through 111f are not limited to the descriptions above and shown in FIGS. 29 through 32 but can be any position as long as formation of the coil pattern 101 and the adjusting resistor 102 and attachment of electronic components are not hindered.

Fifth Embodiment

In the fourth embodiment, the chamfered or recessed portions are provided at or adjacent to the corners of the detection face of the magnetic permeability sensor 100-2, thereby providing the guide portions to guide the operator (or the removal tool) away the coil pattern 101 and the adjusting resistor 102. It is to be noted that, in the description below, the magnetic permeability sensor 100-1 or 100-2 is simply referred to as the magnetic permeability sensor 100.

By contrast, in the fifth embodiment, the guide portions are provided to not the magnetic permeability sensor 100 but the sensor mounting portion 212a. Specifically, chamfered or recessed portions are provided at or adjacent to corners of the sensor mounting portion 212a. This configuration can attain effects similar to those attained in the above-described fourth embodiment.

The fifth embodiment is described in further detail below with reference to FIG. 33, which is a perspective view illustrating an exterior of the developing device 212 according to the present embodiment.

It is to be noted that elements of the fifth embodiment similar to those of the first to third embodiments are given identical or similar reference characters, and thus descriptions thereof omitted. In FIG. 33, the developing device 212 is placed upside down from the posture mounted in the image forming apparatus 200, that is, from the posture of the developing device 212 being used.

Figure 33:
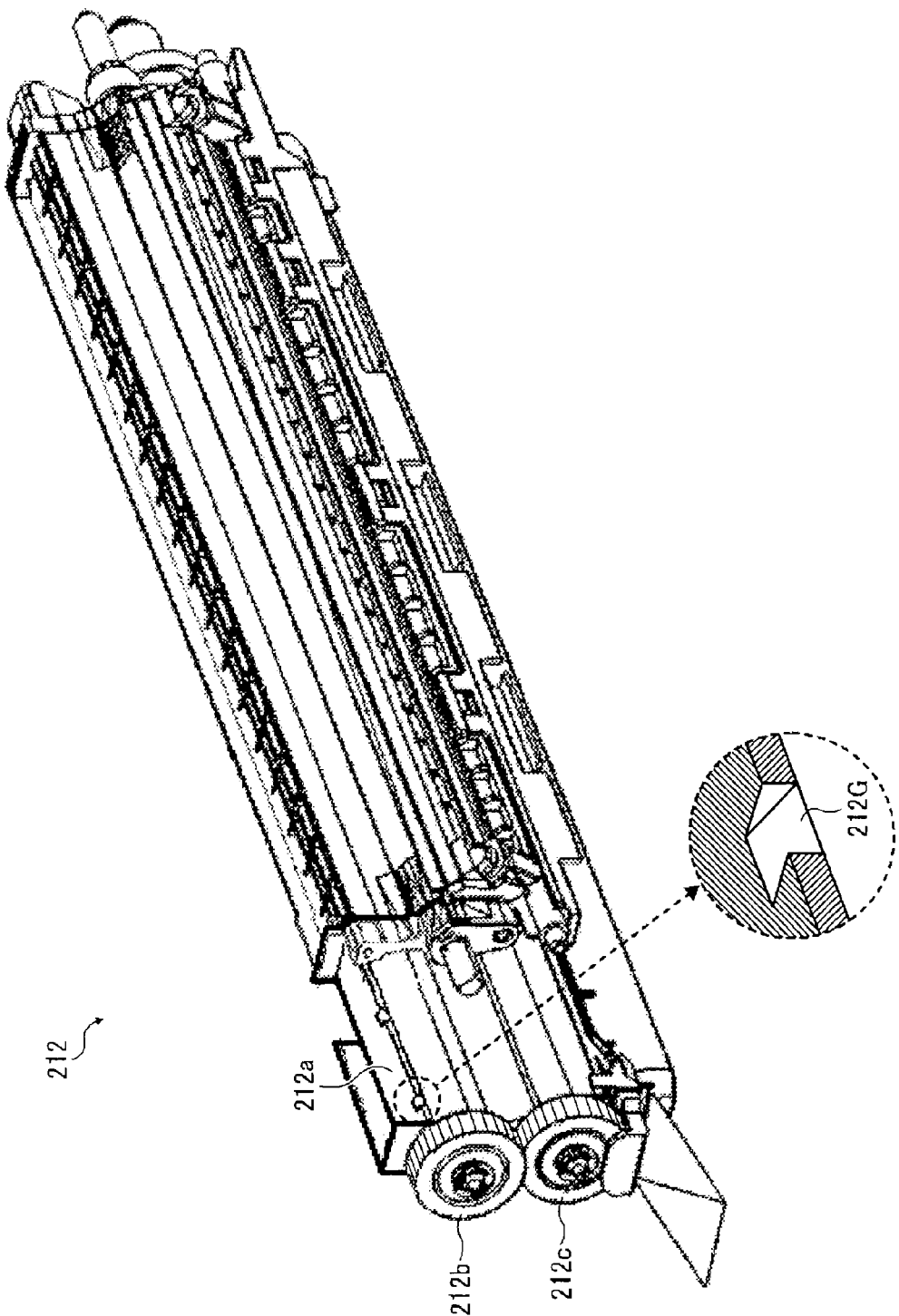
FIG. 33 is a perspective view illustrating a developing device according to an embodiment.

In the configuration shown in FIG. 33, the sensor mounting portion 212a includes, at or adjacent to a corner thereof, a guide portion 212G that is chamfered or recessed. That is, a recess is provided in the face of the sensor mounting portion 212a to which the magnetic permeability sensor 100 is attached. With the developing device 212 thus configured, effects similar to those attained by the fourth embodiment can be attained.

Figure 34:
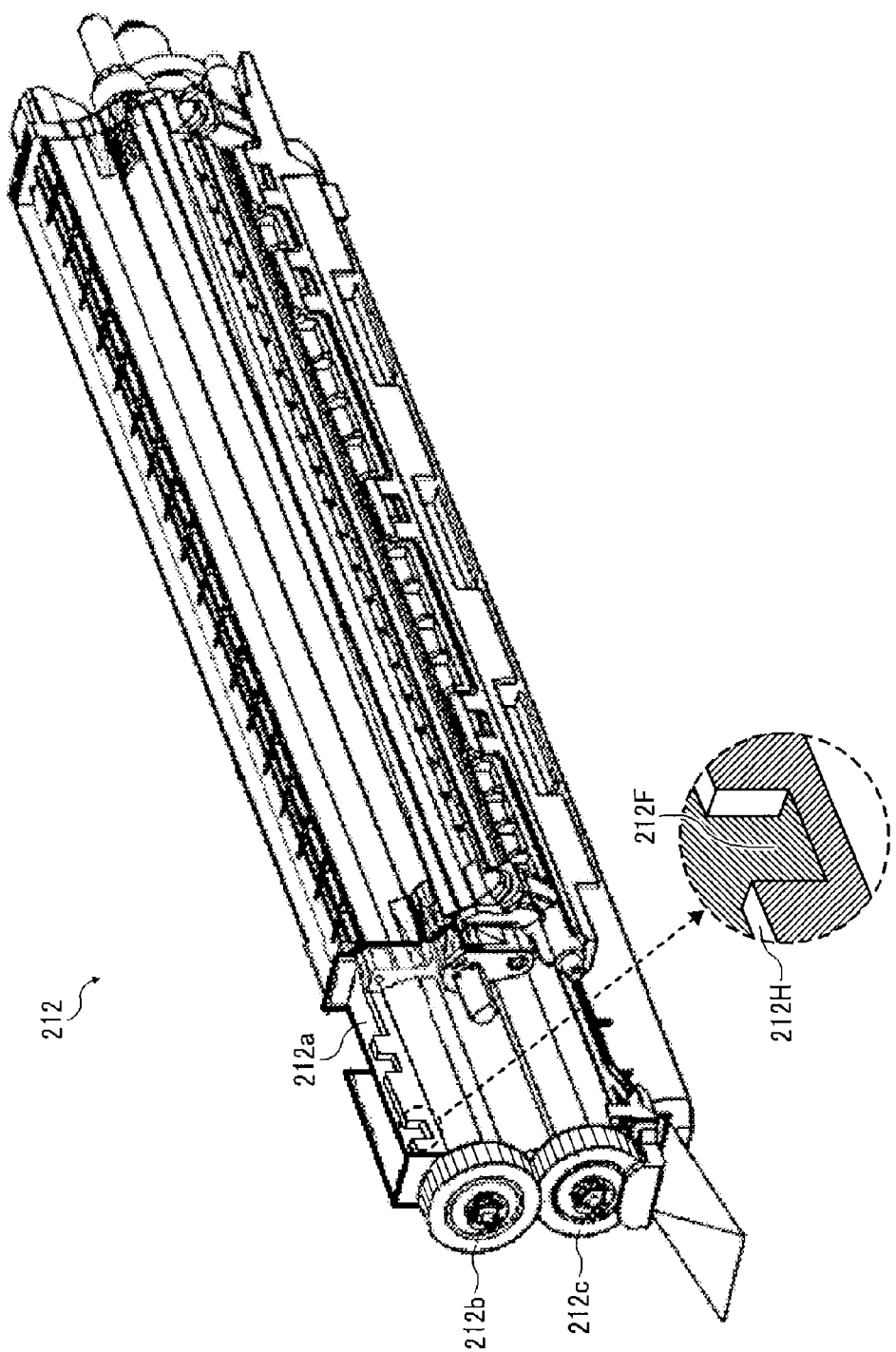
FIG. 34 is a perspective view illustrating a developing device as a variation of that shown in FIG. 33.

FIG. 34 illustrates a variation of the guide portion of the sensor mounting portion 212a.

In FIG. 34, the developing device 212 may include a guide portion 212F that is a recess formed in a wall 212H enclosing the sensor mounting portion 212a. That is, a part of the wall 212H is cut away. It is to be noted that FIG. 34 is similar to FIG. 33 in that the developing device 212 is placed upside down from the posture mounted in the image forming apparatus 200, that is, from the posture of the developing device 212 being used.

With the developing device 212 thus configured, effects similar to those attained by the fourth embodiment can be attained. Additionally, since this configuration inhibits the operator from unintentionally inserting in other portions than the cutout, prevention of damage to the coil pattern 101 and the adjusting resistor 102 by the removal tool can be secured. It is to be noted that the guide portion 212F that is the cutout shown in FIG. 34 may include a chamfered or recessed portion as shown in FIG. 33.

Further, the positions of the guide portions 212G and 212H are not limited to the descriptions above or shown in FIGS. 33 and 34 but can be any position as long as the coil pattern 101 and the adjusting resistor 102 are not damaged by the removal tool in removal of the magnetic permeability sensor 100.

Thus, according to the third to fifth embodiments, the coil pattern 101 and the adjusting resistor 102 can be protected in storage or transport of the magnetic permeability sensor 100 using the LC oscillator circuit including these elements.

It is to be noted that the features of the third to fifth embodiments can adapt to any magnetic permeability detector to detect the magnetic permeability inside the predetermined space opposed to the coil formation face using the LC oscillator circuit including the coil pattern 101 although the descriptions above concern the case in which the magnetic permeability sensor is used to detect the density of toner included in two-component developer including magnetic carrier particles and nonmagnetic toner particles, contained inside the developing device 212 of the electrophotographic image forming apparatus 200.

Further, although the descriptions above concern the magnetic permeability sensor 100 using the LC oscillator circuit including the coil pattern 101 and the adjusting resistor 102, the adjusting resistor 102 is not a requisite in the third through fifth embodiments, and the features of the third to fifth embodiments can adapt to any magnetic permeability detector including an LC circuit including the coil pattern 101.

Yet further, in addition to independently use the third through fifth embodiments, two or all of them may be combined. For example, third and fourth embodiments may be combined. Alternatively, the third and fifth embodiments may be combined. Yet alternatively, the third through fifth embodiments may be combined. The effects described in the third through fifth embodiments can be attained in these cases as well.

Sixth Embodiment

The output from the magnetic permeability sensor employing the LC oscillator circuit described in the first embodiment and the like is an oscillation signal at the frequency corresponding to the magnetic permeability of the space to be detected.

Accordingly, the magnetic permeability is recognized based on the frequency of oscillation signals output from the sensor, and it is necessary to count the number of oscillation signals for a predetermined period.

Therefore, when a processor such as a CPU is used to calculate the magnetic permeability, for example, for detecting the density of toner in the developing device of the image forming apparatus, the count value of the counter to count the sensor output is read according to interrupt signals, and the magnetic permeability is calculated based on the value thus read.

However, if another processing is underway when the processor such as the CPU accesses the counter according to the interrupt signal, there arises a time lag from the interrupt signal to reading out of the counter value.

Consequently, an extra signal output from the sensor is counted during the time lag, obstructing proper calculation of the frequency.

A conceivable approach to address this convenience is, for example, setting the priority of reading out the count value according to the interrupt signal highest. However, behavior of the apparatus may become unstable since the other control processing is postponed.

In view of the foregoing, the present embodiment concerns a configuration to accurately calculate, according to the interrupt signal, the frequency of signals output from the magnetic permeability sensor employing the LC oscillator circuit including the planar coil such as the one according to the first embodiment.

It is to be noted that, in the description below, elements similar to those of the first embodiment are given identical or similar reference characters, and thus descriptions thereof omitted.

Figure 35:
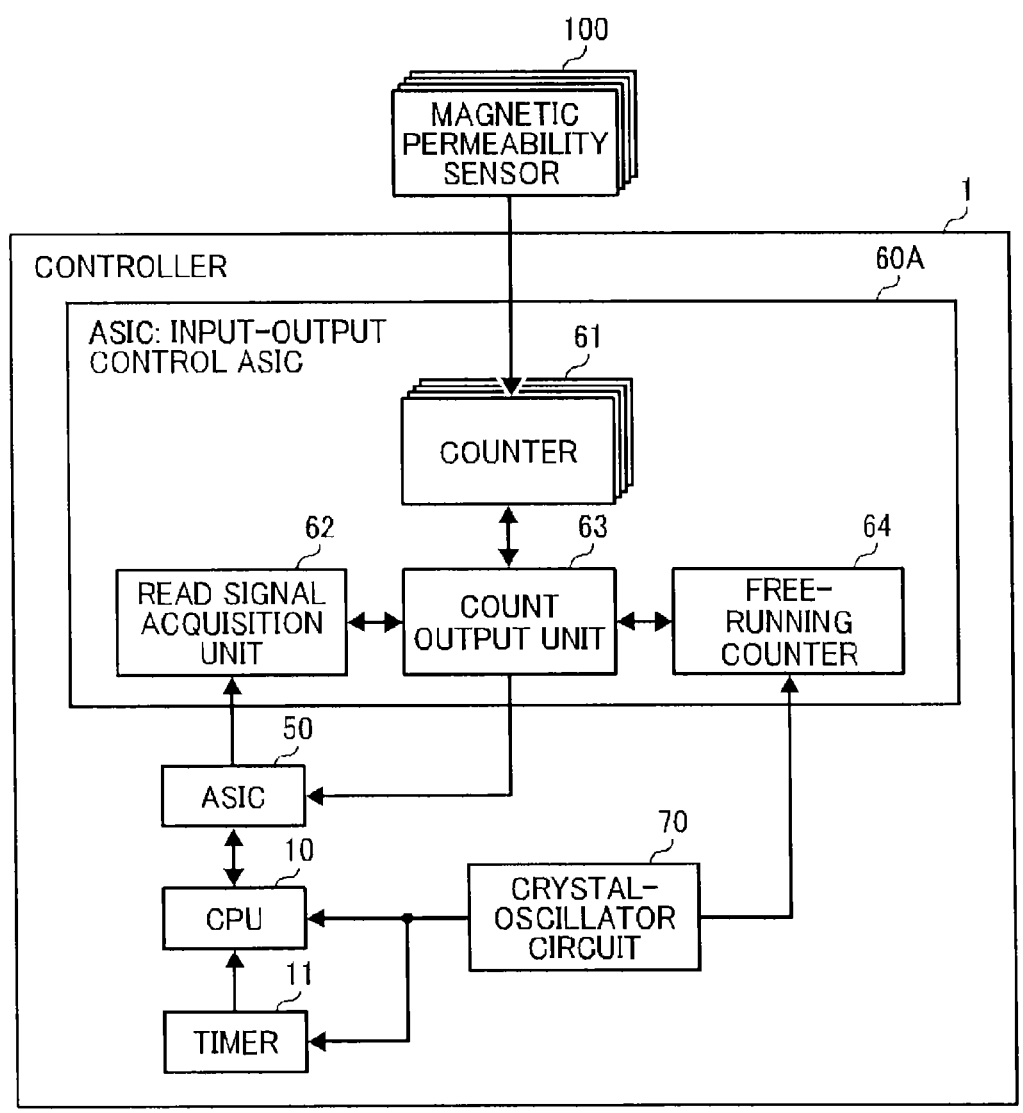
FIG. 35 is a functional block diagram illustrating an input-output control ASIC in a controller according to a sixth embodiment.

FIG. 35 is a functional block diagram illustrating an input-output control ASIC 60A in the controller 1 according to the present embodiment.

In the configuration shown in FIG. 35, the input-output control ASIC 60A includes the counter 61, the read signal acquisition unit 62, the count output unit 63, and a free-running counter 64.

The magnetic permeability sensor 100 according to the present embodiment is an oscillator circuit that outputs rectangular waves at the frequency corresponding to the magnetic permeability in a space to be detected.

The counter 61 increments the count value according to the rectangular wave output from the magnetic permeability sensor 100.

That is, the counter 61 serves as a target signal counter to count the number of the signals whose frequency is to be calculated.

It is to be noted that multiple magnetic permeability sensors 100 are used in the configuration shown in FIG. 35 and multiple counters 61 are used accordingly.

The free-running counter 64 increments the count value according to the reference clock input from the crystal-oscillator circuit 70.

That is, the free-running counter 64 serves as a reference clock counter to count the number of clocks of the reference clock.

Incorporating the free-running counter 64 is one of distinctive features of the present embodiment.

The read signal acquisition unit 62 acquires, via the ASIC 50, a read signal from the CPU 10. The read signal is a command to acquire the count value of the counter 61 and that of the free-running counter 64.

Acquiring the read signal from the CPU 10, the read signal acquisition unit 62 inputs, to the count output unit 63, a signal instructing output of the count value.

According to the signal input by the read signal acquisition unit 62, the count output unit 63 outputs the count value of the counter 61 and that of the free-running counter 64.

In other words, the read signal acquisition unit 62 operates in conjunction with the count output unit 63, together serving as a count value acquisition unit.

As shown in FIG. 35, the controller 1 includes the timer 11. The timer 11 outputs an interrupt signal to the CPU 10 each time the count of reference clock input from the crystal-oscillator circuit 70 reaches a predetermined count. The CPU 10 outputs the read signal in response to the interrupt signal input from the timer 11.

It is to be noted that the CPU 10 has an access to the input-output control ASIC 60A, for example, via a register. Accordingly, the above-described read signal is executed by writing, with the CPU 10, a value in a predetermined register included in the input-output control ASIC 60A. Additionally, output of the count value from the count output unit 63 is executed by storing the count value in a predetermined register included in the input-output control ASIC 60A and acquiring the count value with the CPU 10.

The CPU 10 executes computation according to software program for frequency calculation, thereby constituting a software controller, and the software controller operates in conjunction with hardware such as the input-output control ASIC 60A and the like, thus together constituting a frequency calculation device according to the present embodiment.

As described in the first embodiment, if there are no changes in the density of the magnetic material adjacent to the magnetic permeability sensor 100, the magnetic permeability sensor 100 oscillates at a constant frequency basically. Consequently, the count value of the counter 61 increases constantly with elapse of time as shown in FIG. 4.

Additionally, receiving the interrupt signal from the timer 11, the CPU 10 outputs the read signal to the input-output control ASIC 60 and acquires the count value of the counter 61 and that of the free-running counter 64 at that time. For example, in FIG. 4, at time points $t_1$, $t_2$, $t_3$, $t_4$, and $t_5$, count values aaaah, bbbbh, ccch, ddddh, and AAAAh are acquired respectively.

Acquiring the count values at the respective time points, the CPU 10 calculates the frequency in periods $T_1$, $T_2$, $T_3$, and $T_4$ shown in FIG. 4, respectively. The timer 11 in the present embodiment outputs the interrupt signal when counting the reference clock for an amount equivalent of 2 milliseconds (ms). Accordingly, in principle, oscillation frequency f (Hz) of the magnetic permeability sensor 100 in each of the periods $T_1$, $T_2$, $T_3$, and $T_4$ can be calculated by dividing the count values of the counter 61 in the respective periods with 2 (ms). That is, the duration of 2 ms is a frequency calculation interval at which the frequency of the oscillation signal output from the magnetic permeability sensor 100 is calculated.

Additionally, as shown in FIG. 4, the upper limit of the count of the counter 61 is FFFFh in the present embodiment. Accordingly, in principle, the oscillation frequency f (Hz) in the period $T_4$ can be calculated by dividing with 2 (ms) the sum of the AAAAh and a value obtained by deducting ddddh from FFFFh.

As described in the first embodiment, in the case of FIG. 5, in the input-output control ASIC 60, the counter 61 resets the count value after the count output unit 63 reads out the count value.

In the configuration shown in FIG. 5, the count values acquired at the respective time points are the values counted in the periods $T_1$, $T_2$, $T_3$, and $T_4$, respectively. Accordingly, the CPU 10 can calculate the oscillation frequency f (Hz) by dividing with 2 (ms) the count value acquired at each timing.

In contrast to the first embodiment thus configured, in the sixth embodiment, the interval of calculation (for detecting toner density, for example) is not the fixed value (2 ms, for example) but is based on the counter value of the free-running counter 64.

The inconvenience addressed in the present embodiment is described below.

Figure 36:
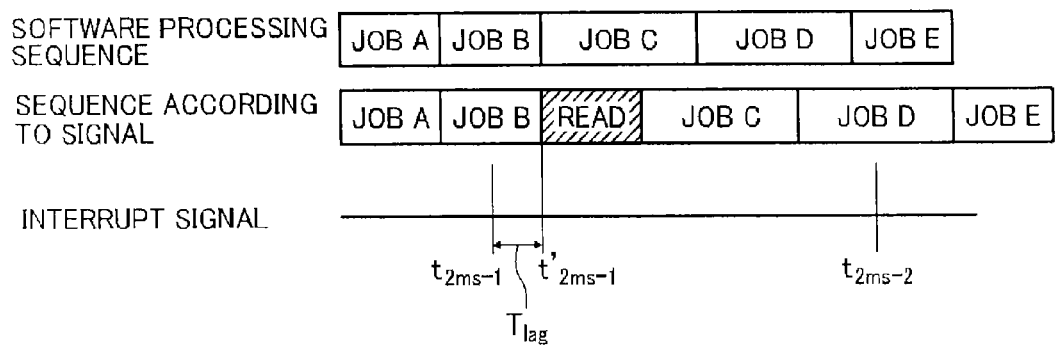
FIG. 36 is a timing chart illustrating relative timings of software processing sequence by a CPU, count of the counter, the interrupt signal, and the read signal.

FIG. 36 is a timing chart illustrating relative timings of software processing sequence by the CPU 10, the count value of the counter 61, the interrupt signal by the timer 11, and the read signal by the CPU 10.

The CPU 10 executes software processing (jobs A, B, C, D, and D in FIG. 36) sequentially in accordance with the operation of the apparatus as shown in FIG. 36. By contrast, when the interrupt signal arises at a time point $t_{2ms-1}$ while the job B is underway, the CPU 10 executes "read" processing at a time point $t'_{2ms-1}$ after the job B is completed.

Therefore, a time lag $T_{lag}$ is present from the generation of the interrupt signal to the start of the read processing. The count value of the counter 61 is incremented also during the time lag $T_{lag}$ according to the output signal from the magnetic permeability sensor 100. That is, although the count value at the time point $t_{2ms-1}$ should be read out according to the interrupt signal, that at the time point $t'_{2ms-1}$ is read out undesirably.

As a result, the frequency of the magnetic permeability sensor 100 is calculated with the combination of the unintended count value and the fixed value (2 ms, for example). That is, the frequency calculated is based on the count value of a period longer than the intended period by the time lag $T_{lag}$ and improper.

The CPU 10 may be configured to discontinue the underway job B and start the read processing promptly in response to the interrupt signal. However, the interruption of the job B may result in malfunction of the apparatus. Additionally, the time required for interrupting the job causes a time lag.

In view of the foregoing, the controller 1 of the magnetic permeability sensor 100 according to the present embodiment uses the count value by the free-running counter 64 in the frequency calculation considering the time lag $T_{lag}$.

Figure 37:
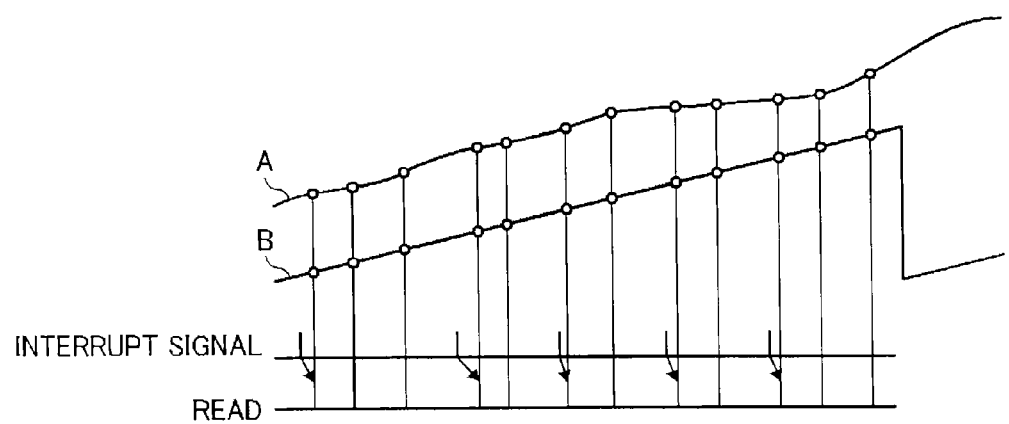
FIG. 37 is a chart for understanding of a principle of determination of the oscillation frequency of the magnetic permeability sensor according to the sixth embodiment.

FIG. 37 is a chart for understanding of a principle of determining the oscillation frequency of the magnetic permeability sensor 100 according to the present embodiment.

In FIG. 37, graph A represents count values of the counter 61, and graph B represents those of the free-running counter 64.

The count value of the counter 61 is incremented according to the frequency of the oscillation signal of the magnetic permeability sensor 100, and the oscillation signal of the magnetic permeability sensor 100 fluctuates depending on the magnetic permeability in the space to be detected. Accordingly, the graph A of count value of the counter 61 in chronological order is a curved line as shown in FIG. 37. By contrast, the count value of the free-running counter 64 is incremented according to the reference clock output from the crystal-oscillator circuit 70, and accordingly the graph B of count value of the free-running counter 64 in chronological order is linear as shown in FIG. 37.

The count values of the counter 61 and the free-running counter 64 are read out in response to the interrupt signal at the predetermined intervals (2 ms, for example).

However, there are cases where the point of time when the CPU 10 reads out the count values is delayed as represented by "read" shown in FIG. 37 from the generation of the interrupt signal, depending on the processing state of the CPU 10 at the time of the interrupt signal.

By contrast, the CPU 10 according to the present embodiment calculates the frequency of the magnetic permeability sensor 100 using the count value of the free-running counter 64 that is read at the same time as the count value of the counter 61. Herein, the frequency $f_i$, of the magnetic permeability sensor 100 during the period from the time point Ti−1 to the time point Ti can be calculated using formula 3 below.

$$f_i = \frac{(N_i - N_{i-1})}{(M_i - M_{i-1})} \cdot f_0 \quad \text{Formula 3}$$

wherein $N_i$ represents the count value of the counter 61, $M_i$ represents the count value of the free-running counter 64, and $f_0$, represents the frequency of the reference clock, all at reading out time points Ti (i represents a given ordinal number of time point T).

According to the formula 3 above, the count number of the counter 61 for the period of a single reference clock can be obtained from the ratio of the count of the counter 61 (i.e., a magnetic permeability counter) and that of the free-running counter 64, expressed as $(N_i-N_{i-1})/M_i-M_{i-1})$.

By multiplying this value with the frequency $f_0$ of the reference clock, the count number of the counter 61 per unit time can be obtained.

That value is the frequency of the magnetic permeability sensor 100 during the target period.

Figure 38:
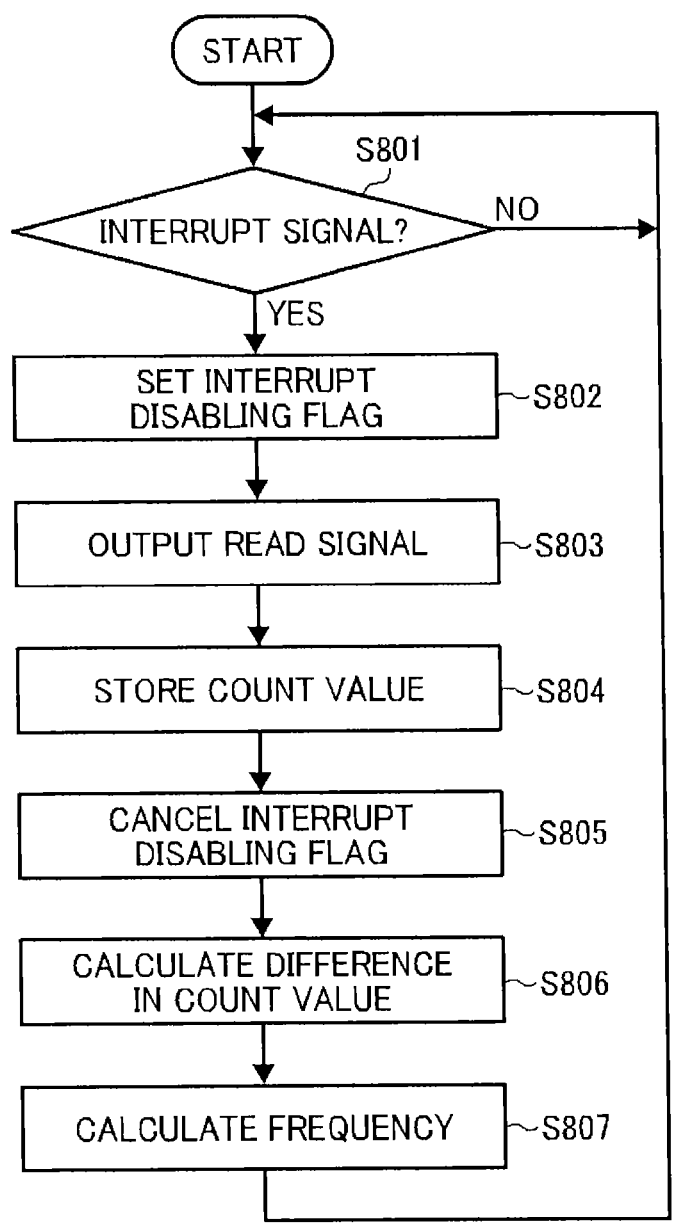
FIG. 38 is a flowchart of calculation of a frequency of signals output from the magnetic permeability sensor according to the sixth embodiment.

Next, descriptions are given below of calculation of frequency of output signals output from the magnetic permeability sensor 100 according to the present embodiment with reference to FIG. 38.

Referring to FIG. 8, the CPU 10 continues a standard operation until an interrupt signal is input from the timer 11 (No at S801). When the timer 11 counts 2 ms and outputs the interrupt signal (Yes at S801), at S802 the CPU 10 sets a flag to disable interruption (hereinafter "interrupt disabling flag").

Then, interruption of other processing is disabled till completion of calculation of frequency of signals output from the magnetic permeability sensor 100.

That is, the CPU 10 serves as an interrupt disabling unit.

After storing various types of count values acquired according to the read signal in a memory such as the random access memory (RAM) at S804, the CPU 10 cancels the interrupt disabling flag at S805.

Storing the count value in the memory, the CPU 10 calculates $(N_i-N_{i-1})$ and $(M_i-M_{i-1})$ in the formula 3, that is, calculates the difference between the previous count value and the current count value of the respective counters at S806. In other words, the CPU 10 calculates the difference in the count values of oscillation signals acquired sequentially at the frequency calculation intervals. Then, as expressed by formula 3, the frequencies of output signals from the respective magnetic permeability sensors 100 are calculated by dividing each of the multiple count values of the counter 61 with the difference from the count value of the free-running counter 64 and multiplying them with the reference clock frequency $f_0$. That is, the CPU 10 that executes computation according to a dedicated program serves as a frequency calculator. The controller 1 according to the present embodiment calculates the frequency by repeating the above-described processing at intervals of 2 ms.

As described above, the controller 1 according to the present embodiment acquires the count value of the oscillation signals of the magnetic permeability sensor 100 in response to the interrupt signal arising at the predetermined intervals and, simultaneously, acquires the count value of the free-running counter 64 incremented at a constant frequency. Then, the frequency of oscillation signals output by the magnetic permeability sensor 100 is calculated based on not the intervals at which the interrupt signal arises but the duration corresponding to the count value of the free-running counter 64.

With this processing, even if the time lag is caused from the generation of the interrupt signal to the count value acquisition, the time lag does not cause error in the frequency calculation since the count value of the free-running counter 64 is also incremented at the constant frequency during the time lag. Thus, according to the sixth embodiment, the frequency of the oscillation signals during the predetermined period can be calculated more accurately.

It is to be noted that, in the description above, although the free-running counter 64 constantly counts the reference clock output from the crystal-oscillator circuit 70, it is an example, and an aspect of the sixth embodiment is to recognize the time lag from when the timer 11 generates the interrupt signal to when the count value of the counter 61 is acquired in response to the read signal and to consider the time lag in the frequency calculation.

Therefore, it is not necessary that the free-running counter 64 counts the reference clock constantly. Alternatively, for example, the free-running counter 64 may start the counting simultaneously with the generation of the interrupt signal. In this case, the count value of the counter 61 acquired in response to the read signal from the CPU 10 is the number of signals counted in the period that is the sum of the interrupt generation interval and the time lag, whereas the count value of the free-running counter 64 is the number of signals counted in the time lag from the generation of interrupt to the read processing.

In this case, the frequency $f_i$, of the signals output from the magnetic permeability sensor 100 can be calculated using formula 4 below, wherein T represents the interrupt generation interval and $M'_i$, represents the count value of the free-running counter 64.

$$f_i = \frac{(N_i - N_{i-1})}{T + \left(\frac{M'_i}{f_0}\right)} \qquad \text{Formula 4}$$

Additionally, the description above is based on an example in which, as described with reference to FIG. 4, the counter 61 accumulatively counts the number of signals output from the magnetic permeability sensor 100 and an example in which the difference from the previously acquired count value is calculated at S806 in FIG. 38 accordingly. However, as described with reference to FIG. 5, the count value may be reset each time the count value is read out in response to the read signal.

In this case, since the count value acquired in response to each read signal is the value of counting started at the previous read processing, it is not necessary to calculate the difference from the previously acquired count value, which is the step at S806 in FIG. 38, and frequency $f_i$ of the signals output from the magnetic permeability sensor 100 can be calculated using formula 5 below.

$$f_i = \frac{N_i}{M_i} \cdot f_0 \qquad \text{Formula 5}$$

Additionally, the description above is an example in which the free-running counter 64 is provided inside the input-output control ASIC 60A and the count output unit 63 acquires the count value of the free-running counter 64 at the same time as the acquisition of the count value of the counter 61. With this configuration, the read timing of the counter 61 and that of the free-running counter 64 can be identical, and the frequency of signals output from the magnetic permeability sensor 100 can be calculated more accurately.

However, it is an example, and a role of the free-running counter 64 is to recognize the time lag from the generation of the interrupt signal to when the count value is practically read out. Accordingly, the counter 64 may be provided outside the input-output control ASIC 60A as long as the count value can be read out simultaneously with the timing at which the count value of the counter 61 is acquired.

In this case, the CPU 10 outputs a read signal to the free-running counter 64 separately from the read signal to the input-output control ASIC 60A. In this operation, it is preferred that the CPU 10 simultaneously output the read signal to the free-running counter 64 and that to the input-output control ASIC 60A. With this operation, the duration of counting by the counter 61 and that by the free-running counter 64 can be equivalent.

Seventh Embodiment

Figure 39:
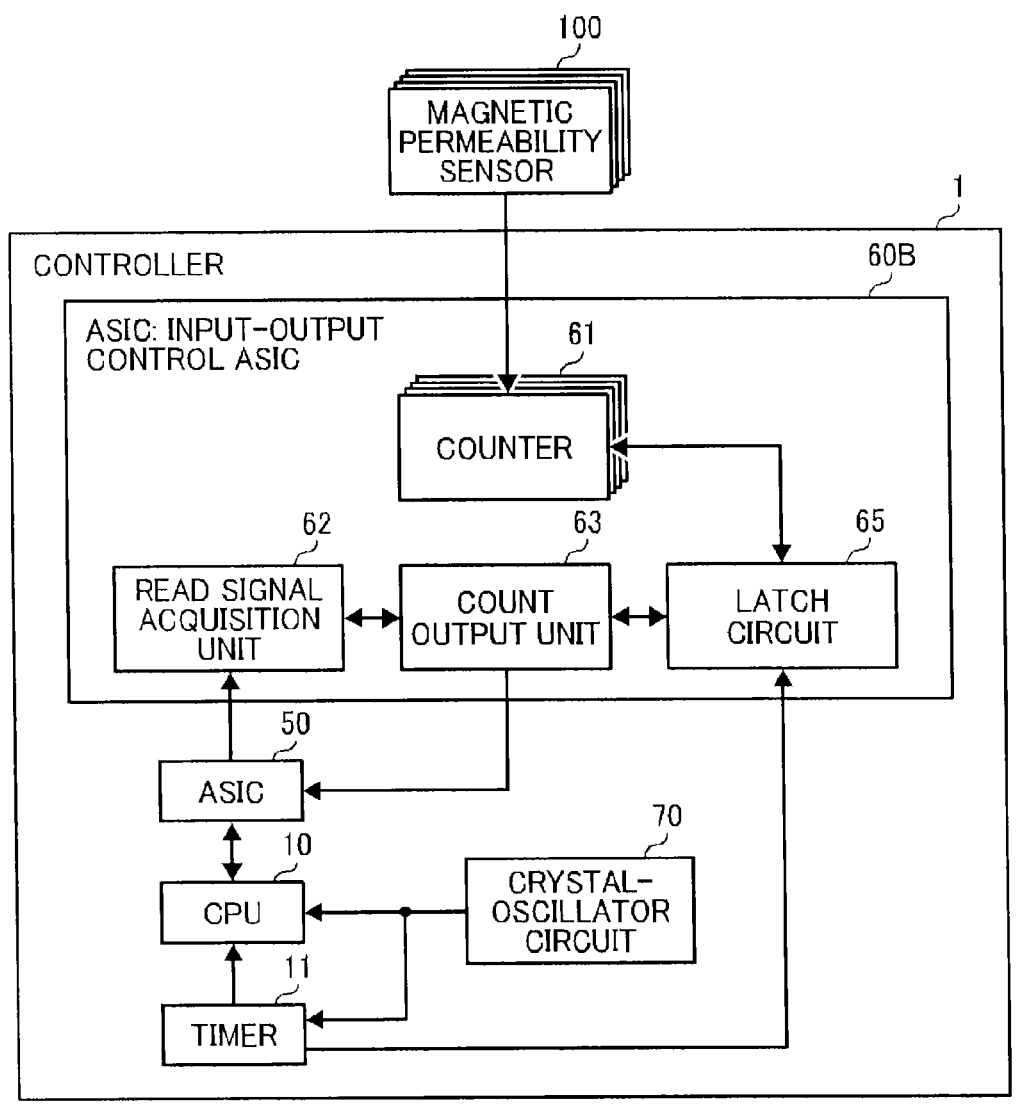
FIG. 39 is a block diagram illustrating circuitry that includes a latch circuit according to a seventh embodiment.

The sixth embodiment is described using an example in which the CPU 10 outputs the read signal in response to the interrupt signal output from the timer 11, and the count values of the counter 61 and the free-running counter 64 are acquired. By contrast, FIG. 39 illustrates an input-output control ASIC 60B that includes a latch circuit 65 to latch the count value of the counter 61 in response to the interrupt signal output from the timer 11. This configuration can obviate the necessity of including the free-running counter 64 described above since the count value latched by the latch circuit 65 is the count value at the timing of the interrupt signal output from the timer 11. Thus, the latch circuit 65 can serve as a latch unit.

In the configuration shown in FIG. 39, the CPU 10 outputs the read signal in response to the interrupt signal output by the timer 11 and acquires the count value latched by the latch circuit 65. The frequency of signals output from the magnetic permeability sensor 100 can be calculated by dividing the count value thus obtained with the interval at which the interrupt signal is generated.

However, such a configuration is on the premise that the interval at which the interrupt signal is generated is determined accurate. By contrast, FIG. 40 illustrates an input-output control ASIC 60C that includes, in addition to the free-running counter 64 to count the number of signals output from the crystal-oscillator circuit 70, the latch circuit 65 to latch the count value of the counter 61 and that of the free-running counter 64 in response to the interrupt signal output from the timer 11.

Figure 40:
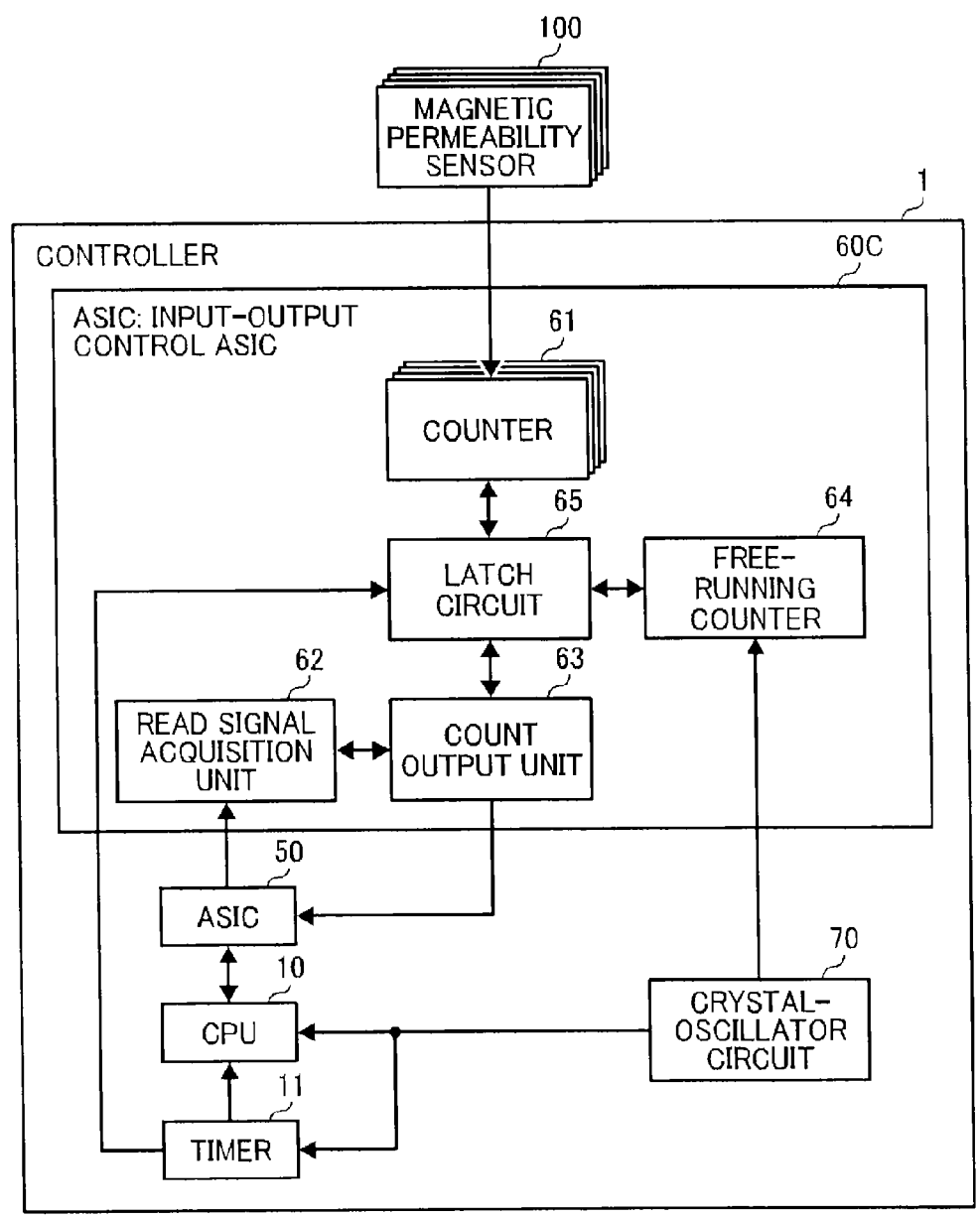
FIG. 40 is a block diagram illustrating circuitry according to the seventh embodiment that includes the latch circuit and a free-running counter.

With the configuration shown in FIG. 40, even if the interval at which the interrupt signal is generated by the timer 11 fluctuates, the frequency of the magnetic permeability sensor 100 can be calculated properly since the calculation is based on the interval at which the count value is practically read out in response to the read signal.

The present specification further includes the following aspects.

Aspect A: A magnetic permeability detector that outputs a signal having a frequency corresponding to a magnetic permeability inside a predetermined space and includes a coil (such as the coil pattern 101) constructed of conducting wire shaped in a planar pattern on a board and has an inductance that changes in accordance with the magnetic permeability inside the predetermined space, a capacitor connected to the coil to constitute a resonance current loop together with the coil, an output terminal to output a signal according to the potential of a part of the resonance current loop, and a planar resistor (such as the adjusting resistor 102) connected serially with the resonance current loop and constructed of a serpentine pattern.

Aspect B: In aspect A, an inductance component generated in the resonance current loop is adjusted by changing the number of serpentine folding of the planar resistor.

Aspect C: In aspect A or B, the coil and the planar resistor are on an identical face of the board, and other components including the capacitor are disposed on a different face of the board.

Aspect D: In aspect C, the other components including the capacitor are disposed outside an area on the back of an area occupied by the coil and the planar resistor.

Aspect E: In any of aspects A through D, the number of serpentine folding is adjusted so that temperature of an extreme value in resonance frequency changes of the resonance current loop corresponding to temperature changes of the location where the magnetic permeability sensor is provided matches temperature of an extreme value in oscillation frequency changes, corresponding to temperature changes, of an oscillator circuit generating a clock to operate a counter to count signals output from the output terminal.

Aspect F: A developer density detector to detect the density of developer to develop an electrostatic latent image in an image forming apparatus includes a coil that is a planar pattern disposed on a board and has an inductance that changes in accordance with the magnetic permeability inside a predetermined space in which developer is contained, a capacitor connected to the coil to form a resonance current loop together with the coil, an output terminal to output a signal according to the potential of a part of the resonance current loop, and a planar resistor connected serially with the resonance current loop and constructed of a serpentine pattern, and the developer density detector is disposed with a planar portion in which the coil is present opposing to the space in which developer is contained.

Aspect G: A developing device to develop an electrostatic latent image in an image forming apparatus includes a developer container to contain developer and a developer density detector to detect the density of developer in the developer container. The density detector includes a coil that is a planar pattern disposed on a board and has an inductance that changes in accordance with the density of developer inside the developer container, a capacitor connected to the coil to form a resonance current loop, an output terminal to output a signal according to the potential of a part of the resonance current loop, and a planar resistor connected serially with the resonance current loop and constructed of a serpentine pattern, and the developer density detector is disposed with a planar portion in which the coil is present opposing to the developer container.

Aspect H: An image forming apparatus to develop an electrostatic latent image formed on a photoreceptor includes a developer container to contain developer and a developer density detector to detect the density of developer in the developer container. The density detector includes a coil that is a planar pattern disposed on a board and has an inductance that changes in accordance with the density of developer inside the developer container, a capacitor connected to the coil to form a resonance current loop, an output terminal to output a signal according to the potential of a part of the resonance current loop, and a planar resistor connected serially with the resonance current loop and constructed of a serpentine pattern, and the developer density detector is disposed with a planar portion in which the coil is present opposing to the developer container.

Aspect I: A method of detecting the magnetic permeability inside the predetermined space according to a signal whose frequency changes in accordance with the magnetic permeability inside the predetermined space includes a step of forming a planar coil pattern on a board with wire whose inductance changes depending on the magnetic permeability inside the predetermined space, a step of connecting the coil and a capacitor to form a resonance current loop, a step of connecting a planar serpentine pattern resistor serially with the resonance current loop, and a step of outputting a signal in accordance with potential of a part of the resonance current loop.

Aspect J: A method of detecting the density of developer to develop an electrostatic latent image in an image forming apparatus includes a step of forming a planar coil pattern on a board with wire whose inductance changes depending on the magnetic permeability inside the predetermined space, a step of connecting the coil and a capacitor to form a resonance current loop, a step of connecting a planar serpentine pattern resistor serially with the resonance current loop, and a step of outputting a signal in accordance with potential of a part of the resonance current loop.

Aspect K: Aspect K concerns a magnetic permeability detector that outputs a signal having a frequency corresponding to a magnetic permeability inside a predetermined space. The magnetic permeability detector includes a coil constructed of a planar pattern on a board and has an inductance that changes in accordance with the magnetic permeability inside the predetermined space, a capacitor connected to the coil to form a resonance current loop together with the coil, an output terminal to output a signal according to the potential of a part of the resonance current loop, and an adhesive layer to attach the magnetic permeability detector to a wall of the predetermined space. The adhesive layer covers an area occupied by the coil on the board, and the magnetic permeability detector is attached to the wall with the coil formation face opposing to the predetermined space.

Aspect L: In aspect K, further provided is a guide portion to guide a removal tool to apply force to the magnetic permeability detector attached with adhesion force of the adhesive layer with the coil formation face opposing to the predetermined space to remove the magnetic permeability detector from the wall.

Aspect M: In aspect K or L, further provided is a guide portion to guide a removal tool to apply force to the magnetic permeability detector attached with adhesion force of the adhesive layer to avoid the area occupied by the coil on the board.

Aspect N: In any of aspects K through M, adhesive force between the adhesive layer and the coil formation face is greater than adhesive force between the adhesive layer and the wall opposing to the coil formation face.

Aspect O: A developing device to developer an electrostatic latent image in an image forming apparatus includes a developer container to contain developer to develop the electrostatic latent image and a toner density detector to detect the density of toner of developer contained in the developer container. The toner density detector includes a coil constructed of a planar pattern provided on a board and has an inductance that changes in accordance with the magnetic permeability inside the predetermined space, a capacitor connected to the coil to form a resonance current loop, an output terminal to output a signal according to the potential of a part of the resonance current loop, and an adhesive layer covering an area occupied by the coil on the board to attach the toner density detector to a wall of the predetermined space with the coil formation face opposing to the predetermined space.

Aspect P: In aspect O, further provided is a guide portion to guide a removal tool to apply force to the toner density detector attached with adhesion force of the adhesive layer with the coil formation face opposing to the predetermined space to remove the toner density detector from the wall.

Aspect Q: In the developing device according to aspect O or P, further provided is a guide portion to guide a removal tool to apply force to the toner density detector attached with adhesion force of the adhesive layer to avoid the area occupied by the coil on the board.

Aspect R: In the developing device according to any of aspects O through Q, adhesive force between the adhesive layer and the coil formation face is greater than adhesive force between the adhesive layer and the wall opposing to the coil formation face.

Aspect S: In the developing device according to any of aspects O through R, the developer container is further provided with a guide portion to guide a removal tool to apply force to the toner density detector attached with adhesion force of the adhesive layer with the coil formation face opposing to the predetermined space to remove the toner density detector from the wall.

Aspect T: In the developing device according to any of aspects O through S, the developer container is further provided with a guide portion to guide a removal tool to apply force to the toner density detector attached with adhesion force of the adhesive layer to avoid the area occupied by the coil on the board.

Aspect U: A frequency calculation device to calculate the frequency of oscillation signals includes a target signal counter to count the number of the oscillation signals, a reference clock counter to count the clock number of the reference clock, a count value acquisition unit to acquire the count value of the oscillation signals and that of the reference clock in response to an interrupt signal generated at an interval that is a frequency calculation interval between which the frequency of the oscillation signals is calculated, and a frequency calculator to recognize the frequency calculation interval based on the count value of the reference clock and calculate the frequency of the oscillation signal during the recognized frequency calculation interval using the count value of the oscillation signals.

Aspect V: In the aspect U, the reference clock counter counts the clock number of the reference clock regardless of generation of the interrupt signal, and the frequency calculator calculates the frequency of the oscillation signal based on a ratio between the count value of the oscillation signal and that of the reference clock.

Aspect W: In aspect U or V, the frequency calculator acquires the count value of the oscillation signals during the recognized frequency calculation interval by calculating the difference in the count values of oscillation signals acquired sequentially at the frequency calculation interval, and then calculates the frequency of the oscillation signals.

Aspect X: In aspect U or V, the count value generated by the target signal counter is reset each time the count value of the oscillation signals is acquired in response to the interrupt signal, and the frequency calculator acquires the count value of the oscillation signals in response to the interrupt signal as the count value of the oscillation signals during the frequency calculation interval and then calculates the frequency of the oscillation signals.

Aspect Y: In any of aspects U through X, further provided is an interrupt disabling unit to disable any processing triggered by another interrupt signal during a period from generation of the interrupt signal generated at the frequency calculation interval to acquisition completion of the count value of the oscillation signals and that of the reference clock.

Aspect Z: In any of aspects U through X, further provided is a latch unit to latch, in response to the interrupt signal generated at the frequency calculation intervals, the count value generated by the target signal counter and that generated by the reference clock counter, and the count value acquisition unit acquires the count values latched by the latch unit.

Aspect AA: An image forming apparatus to develop an electrostatic latent image formed on a photoreceptor includes a developer container to contain developer and a developer density detector to detect the density of developer in the developer container. The density detector includes a sensor to output an oscillation signal having a frequency corresponding to the density of developer in the developer container, a target signal counter to count the number of the oscillation signals, a reference clock counter to count the clock number of the reference clock, a count value acquisition unit to acquire the count value of the oscillation signals and that of the reference clock in response to an interrupt signal generated at an interval that is a frequency calculation interval between which the frequency of the oscillation signals is calculated, and a frequency calculator to recognize the frequency calculation interval based on the count value of the reference clock and calculate the frequency of the oscillation signal using the count value of the oscillation signals.

Aspect AB: A method to calculate the frequency of oscillation signals includes a step of acquiring the count value of the oscillation signals and that of the reference clock in response to an interrupt signal generated at an interval that is a frequency calculation interval between which the frequency of the oscillation signals is calculated, a step of recognizing the frequency calculation interval based on the count value of the reference clock, and a step of calculating the frequency of the oscillation signal during the recognized frequency calculation interval using the count value of the oscillation signals.

Numerous additional modifications and variations are possible in light of the above teachings. It is therefore to be understood that, within the scope of the appended claims, the disclosure of this patent specification may be practiced otherwise than as specifically described herein.

What is claimed is:

1. A detector comprising:
an oscillator circuit including a coil configured to detect magnetic permeability; and
a resistor connected in series with the coil, wherein
a first resistance of the resistor is added to a second resistance of the coil,
the second resistance of the coil is in series with the resistor, and
the resistor includes conducting wire.

2. The detector according to claim 1, further comprising a board, and a capacitor,
wherein the coil, the capacitor, and the resistor are provided on the board.

3. The detector according to claim 2, wherein the resistor is connected in parallel to the capacitor.

4. The detector according to claim 2, wherein the resistor is planar, and the conducting wire is printed on the board.

5. The detector according to claim 2, wherein the coil is planar and includes other conducting wire printed on the board.

6. The detector according to claim 2, wherein the coil and the resistor are provided on a first face of the board.

7. The detector according to claim 6, wherein the capacitor is provided on a second face of the board opposite the first face on which the coil and the resistor are printed, and an output terminal is provided on the second face.

8. The detector according to claim 4, wherein the conducting wire is bent multiple times in a predetermined direction on the board.

9. The detector according to claim 8, wherein adjacent segments of the bent conducting wire are parallel to each other.

10. The detector according to claim 4, wherein the conducting wire is bent into a symmetrical shape.

11. A developing device comprising:
a developer container to contain a developer; and
a developer density detector to detect a density of the developer in the developer container, the developer density detector including the detector according to claim 1,
wherein the coil generates a magnetic flux in a predetermined direction by a current flowing through the coil upon application of a power supply voltage to the developer density detector,
wherein the developer density detector further comprises an output terminal to output a signal having a frequency corresponding to the magnetic permeability in a range of action of the magnetic flux, and
wherein the developer density detector is attached to the developing device so that the magnetic flux acts on the developer container.

12. An image forming apparatus comprising:
an image bearer on which an electrostatic latent image is formed;
a controller including the oscillator circuit according to claim 1 to generate a reference clock; and
the detector according to claim 1, the detector further comprising an output terminal to output a signal having a frequency corresponding to the magnetic permeability in a range of action of a magnetic flux, wherein
the signal output from the output terminal is counted by a counter operating based on the reference clock, and
the first resistance of the resistor is set to make a temperature characteristic of the frequency of the signal output from the output terminal closer to a temperature characteristic of the oscillator circuit that outputs the reference clock.

13. A detector comprising:
a coil having a resistance;
an oscillator circuit including the coil configured to detect magnetic permeability, the oscillator circuit having a resistance which includes the resistance of the coil; and
a resistor connected in series with the coil,
wherein a resistance of the resistor is included in the resistance of the oscillator circuit, and
wherein the resistor includes conducting wire.

14. The detector according to claim 13, further comprising a board, and a capacitor, wherein the coil, the capacitor, and the resistor are provided on the board.

15. The detector according to claim 14, wherein the resistor is connected in parallel to the capacitor.

16. The detector according to claim 14, wherein the resistor is planar, and the conducting wire is printed on the board.

17. The detector according to claim 14, wherein the coil is planar and includes other conducting wire printed on the board.

18. The detector according to claim 14, wherein the coil and the resistor are provided on a first face of the board.

19. The detector according to claim 18, wherein the capacitor is provided on a second face of the board opposite the first face on which the coil and the resistor are printed, and an output terminal is provided on the second face.

20. The detector according to claim 16, wherein the conducting wire is bent multiple times in a predetermined direction on the board.

21. The detector according to claim 20, wherein adjacent segments of the bent conducting wire are parallel to each other.

22. The detector according to claim 16, wherein the conducting wire is bent into a symmetrical shape.

23. A developing device comprising:
a developer container to contain a developer; and
a developer density detector to detect a density of the developer in the developer container, the developer density detector including the detector according to claim 13,
wherein the coil generates a magnetic flux in a predetermined direction by a current flowing through the coil upon application of a power supply voltage to the developer density detector,
wherein the developer density detector further comprises an output terminal to output a signal having a frequency corresponding to the magnetic permeability in a range of action of the magnetic flux, and
wherein the developer density detector is attached to the developing device so that the magnetic flux acts on the developer container.

24. An image forming apparatus comprising:
an image bearer on which an electrostatic latent image is formed;
a controller including the oscillator circuit according to claim 13 to generate a reference clock; and
the detector according to claim 13, the detector further comprising an output terminal to output a signal having a frequency corresponding to the magnetic permeability in a range of action of a magnetic flux;
wherein the signal output from the output terminal is counted by a counter operating based on the reference clock, and the resistance of the resistor is set to make a temperature characteristic of the frequency of the signal output from the output terminal closer to a temperature characteristic of the oscillator circuit that outputs the reference clock.

* * * * *